United States Patent
Chen

(10) Patent No.: US 12,221,418 B2
(45) Date of Patent: Feb. 11, 2025

(54) MONTELUKAST BERBERINE QUATERNARY AMMONIUM SALT COMPOUND AND DOUBLE SALT COMPOSITION, AND SYNTHESIS METHOD THEREFOR AND USE THEREOF

(71) Applicant: EYE HOSPITAL, WENZHOU MEDICAL UNIVERSITY, Wenzhou (CN)

(72) Inventor: Wei Chen, Wenzhou (CN)

(73) Assignee: EYE HOSPITAL, WENZHOU MEDICAL UNIVERSITY, Wenzhou (CN)

( * ) Notice: Subject to any disclaimer, the term of this patent is extended or adjusted under 35 U.S.C. 154(b) by 0 days.

(21) Appl. No.: 18/708,597

(22) PCT Filed: Nov. 16, 2022

(86) PCT No.: PCT/CN2022/132329
§ 371 (c)(1),
(2) Date: May 9, 2024

(87) PCT Pub. No.: WO2023/088319
PCT Pub. Date: May 25, 2023

(65) Prior Publication Data
US 2024/0336569 A1    Oct. 10, 2024

(30) Foreign Application Priority Data
Nov. 16, 2021 (CN) .......................... 202111358162.9

(51) Int. Cl.
| A61K 31/43 | (2006.01) |
| A61K 31/4375 | (2006.01) |
| A61K 31/47 | (2006.01) |
| A61P 29/00 | (2006.01) |
| C07D 215/18 | (2006.01) |
| C07D 455/03 | (2006.01) |

(52) U.S. Cl.
CPC ........ C07D 215/18 (2013.01); A61K 31/4375 (2013.01); A61K 31/47 (2013.01); A61P 29/00 (2018.01); C07D 455/03 (2013.01)

(58) Field of Classification Search
CPC ................................ A61K 31/43; A61K 31/47
USPC ........................................................ 514/280
See application file for complete search history.

(56) References Cited

U.S. PATENT DOCUMENTS
2010/0292251 A1    11/2010    Shimpi et al.

FOREIGN PATENT DOCUMENTS

| CN | 101747405 A | 6/2010 |
| CN | 101935334 A | 1/2011 |
| CN | 103193772 A | 7/2013 |
| CN | 103204850 A | 7/2013 |
| CN | 112851660 A | 5/2021 |
| CN | 116135855 A | 5/2023 |
| WO | 2009113087 A1 | 9/2009 |

OTHER PUBLICATIONS

International search report received in the corresponding international application PCT/CN2022/132329, mailed Feb. 10, 2023.
Written opinion of ISA received in the corresponding international application PCT/CN2022/132329, mailed Feb. 10, 2023.

*Primary Examiner* — Raymond J Henley, III
(74) *Attorney, Agent, or Firm* — Kilpatrick Townsend & Stockton LLP

(57) ABSTRACT

Disclosed is a montelukast berberine double salt or composition with anti-inflammatory, antibacterial and immunomodulatory effects. Particularly, disclosed are a montelukast berberine quaternary ammonium salt with a structure as represented by formula (I), a double salt or a composition, a solvate, a hydrate, an isotope substitution or an isomer thereof.

20 Claims, 2 Drawing Sheets
Specification includes a Sequence Listing.

MONTELUKAST BERBERINE QUATERNARY AMMONIUM SALT COMPOUND AND DOUBLE SALT COMPOSITION, AND SYNTHESIS METHOD THEREFOR AND USE THEREOF

PRIORITY CLAIM

The present application claims priority to Chinese Patent Application No. 202111358162.9, entitled "Montelukast Berberine Quaternary Ammonium Salt Compound and Double Salt Composition, and Synthesis Method Therefor and Use Thereof", filed on Nov. 16, 2021, which said application is incorporated by reference in its entirely herein.

REFERENCE TO AN ELECTRONIC SEQUENCE LISTING

The contents of the electronic sequence listing (115436-1443355-000200US.xml; Size: 10,048 bytes; and Date of Creation: Oct. 10, 2024) is herein incorporated by reference in its entirety.

TECHNICAL FIELD

The present invention belongs to the field of medicinal chemistry, and specifically includes a novel montelukast berberine quaternary ammonium salt compound having a structure as represented by formula (I), a double salt composition, a composition including such compound, as well as applications of such compound, composition and double salt in the preparation of drugs for prevention, alleviation and/or treatment of diseases related to allergy, inflammations, vascular malformation, infections, immunity and others, such as ulcerative colitis, rhinitis, asthma, vascular malformation/vasculitis, dry eye, eye infections and inflammations.

BACKGROUND

Berberine is an isoquinoline alkaloid extracted from the roots and barks of *Coptis chinensis* Franch. Berberine is a main ingredient of traditional Chinese medicine *Coptis chinensis*, which is previously considered to be not easy to absorb after oral administration, and is effective for intestinal infections, ocular conjunctivitis, purulent otitis media and others caused by *Escherichia coli* and *Staphylococcus aureus*, and is mainly used for the treatment of intestinal infections in clinical practice. In recent years, berberine has been found to have pharmacological effects such as blood sugar reduction, blood lipid reduction and anti-inflammation. It has been found under study that in animal models of atherosclerosis, berberine treatment can significantly reduce the levels of LDL-C and TC in serum, inhibit the secretion of inflammatory factor IL-6, reduce the content of ALP, BMP-2, OPG, OCN, RUNX2 and calcium in serum and tissues, inhibit the vasculitic infiltration and improve the plaque stability. It has been found at the same time that berberine has a certain anti-angiogenic effect, which is mainly regulated by inhibiting various pro-inflammatory and pro-angiogenic factors, mainly including HIF, VEGF, COX-2, NO, NF-κB, pro-inflammatory cytokines and the like. An anti-inflammatory mechanism of berberine may be summarized as affecting the balance between immune cells Treg and Th17 through the regulation of pathways of NF-κB, MAPK and PPARγ signaling, and inhibiting the secretion and expression of inflammatory factors such as IL-1β, IL-6, IL-8, IL-17, TNF-α, and ICAM-1, thereby hindering the adhesion and migration of leukocytes and endothelium, reducing the neutrophil infiltration, promoting the apoptosis, and alleviating tissue damages. Current clinical studies have preliminarily found that berberine plays a certain therapeutic role in inflammation-related diseases such as metabolism and autoimmunity.

In the past, berberine was generally used as hydrochloride due to poor water solubility, low oral bioavailability and other reasons. However, berberine hydrochloride, which is widely used, has poor water solubility and fat solubility, accompanied with malabsorption in the gastrointestinal tract, resulting in low oral bioavailability, which affects its systemic therapeutic effect.

Montelukast or a sodium salt thereof is a strongly selective leukotriene receptor antagonist. A metabolite of leukotrienes arachidonic acid 5-lipoxidase is a potent inflammatory transmitter that mediates a range of immune responses. Montelukast may be highly selectively bound with a leukotriene receptor to block an inflammatory effect of leukotrienes, thereby exerting anti-inflammatory and anti-allergic effects, and is widely used in the treatment of a variety of respiratory allergic diseases. Recent animal and clinical studies have found that montelukast also has a good anti-oxidation function.

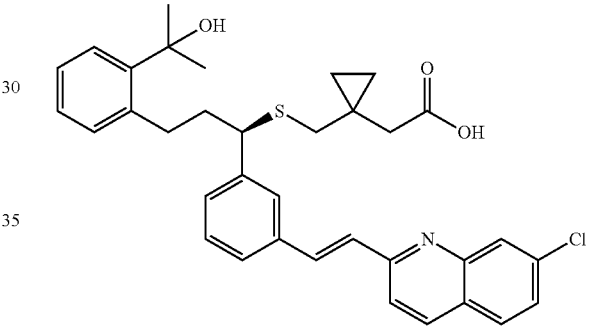

Montelukast

Although berberine and montelukast may have synergistic effects in anti-inflammatory, anti-infective and immunomodulatory effects, no previous studies have reported in this regard. The applicant innovatively prepared berberine and montelukast into a corresponding berberine montelukast salt, which not only improved the solubility between the berberine and the montelukast and increased the solution stability and bioavailability of the berberine montelukast salt, but also showed stronger anti-inflammatory effects, reduced side effects, especially avoided the potential risk of hyperchloremia of hydrochloride, and improved the safety.

The inventors have unexpectedly found that part of a novel quaternary ammonium salt compound having a structure as represented by formula (I) of the present invention or a double salt composition thereof not only improves the solubility of berberine/montelukast, improves the solubility between the berberine and the montelukast and increases the solution stability and bioavailability thereof, but also shows stronger anti-inflammatory effects, reduces side effects, especially avoids the potential risk of hyperchloremia of berberine hydrochloride, and improves the safety, and is thus more suitable for preparation of drugs or various preparations for prevention, alleviation and/or treatment of diseases related to allergy, inflammations, vascular malformation,

3 infections, immunity and others, such as ulcerative colitis, rhinitis, asthma, vascular malformation/vasculitis, dry eye, eye infections and inflammations.

SUMMARY OF THE INVENTION

An object of the present invention is to provide a quaternary ammonium salt conjugated compound as represented by formula (I) or a pharmaceutically acceptable salt, a solvate, a composition, an enantiomer and an isotope substitution or a double salt thereof,

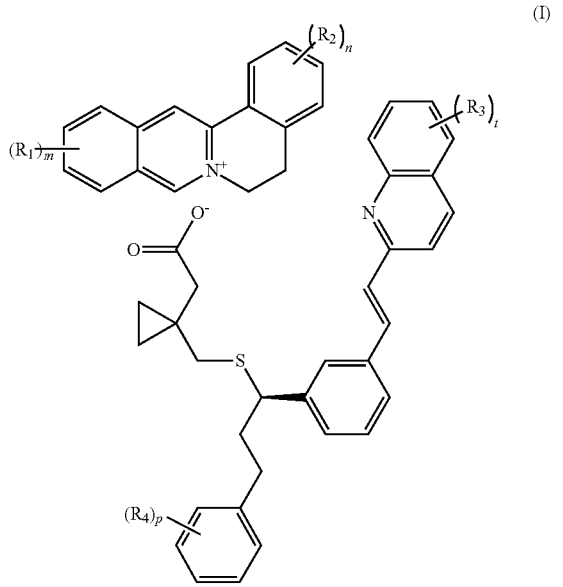

(I)

wherein
R$_1$ and R$_2$ are independently selected from hydrogen, deuterium, halogen, —CN, C$_{1-10}$ alkyl, C$_{2-10}$ alkenyl, C$_{2-10}$ alkynyl, C$_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the C$_{1-10}$ alkyl, C$_{2-10}$ alkenyl, C$_{2-10}$ alkynyl, C$_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally optimally substituted by one to more substituent groups; and the substituent groups are arbitrarily selected from hydrogen, deuterium, halogen, alkyl, haloalkyl, alkoxyl, alkylamino, O=, CN, OH, C$_{3-10}$ saturated or partially saturated cycloalkyl, C$_{3-10}$ saturated or partially saturated heterocyclyl, 6-10 membered aryl and 5-8 membered heteroaryl; or
any two adjacent R$_1$ or any two adjacent R$_2$ form 5-6 membered aryl or heteroaryl, 3-8 membered saturated or partially saturated cycloalkyl, 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, CF$_3$, OH, OCH$_3$, and OCH$_2$CH$_3$;
R$_3$ and R$_4$ are independently selected from hydrogen, deuterium, halogen, —CN, C$_{1-10}$ alkyl, C$_{2-10}$ alkenyl, C$_{2-10}$ alkynyl, C$_{1-10}$ alkoxyl, 6-10 membered aryl, 5-8 membered heteroaryl, 3-8 membered saturated or par-

4 tially saturated cycloalkyl and 3-8 membered saturated or partially saturated heterocyclyl, wherein the C$_{1-10}$ alkyl, C$_{2-10}$ alkenyl, C$_{2-10}$ alkynyl, C$_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally optimally substituted by one to more substituent groups; and the substituent groups are arbitrarily selected from hydrogen, deuterium, halogen, alkyl, haloalkyl, alkoxyl, alkylamino, O=, CN, OH, C$_{3-10}$ saturated or partially saturated cycloalkyl, C$_{3-10}$ saturated or partially saturated heterocyclyl, 6-10 membered aryl and 5-8 membered heteroaryl; or
any two adjacent R$_3$ or any two adjacent R$_4$ form 5-6 membered aryl or heteroaryl, 3-8 membered saturated or partially saturated cycloalkyl, and 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, CF$_3$, OH, OCH$_3$, and OCH$_2$CH$_3$;
heteroatoms in the heteroaryl and heterocyclyl represent any heteroatom independently selected from O, N, S, and P, and isotopes thereof;
the halogen is arbitrarily independently selected from F, Cl, Br, and I, and isotopes thereof; and
m is an integer arbitrarily selected from 0, 1, 2, 3 and 4;
n is an integer arbitrarily selected from 0, 1, 2, 3 and 4;
P is an integer arbitrarily selected from 0, 1, 2, 3, 4 and 5; and
t is an integer arbitrarily selected from 0, 1, 2, 3, 4 and 5.

In a scheme of the present invention, the quaternary ammonium salt conjugated compound or the pharmaceutically acceptable salt, the solvate, the enantiomer and the isotope substitution, the composition or the double salt thereof has a structure as represented by formula (IA),

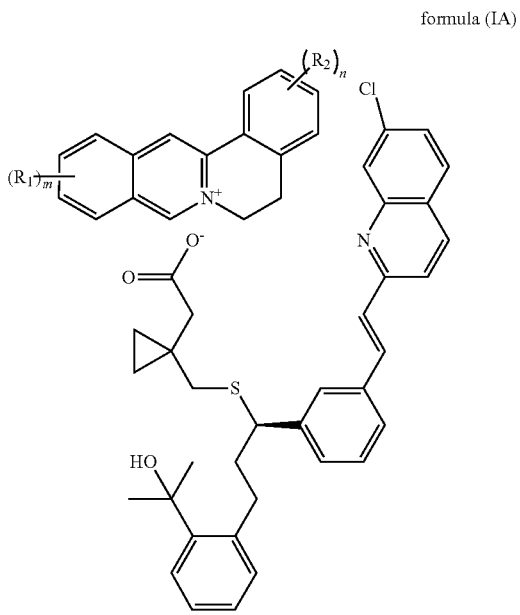

formula (IA)

wherein
R$_1$ and R$_2$ are independently selected from hydrogen, deuterium, halogen, —CN, C$_{1-10}$ alkyl, C$_{2-10}$ alkenyl, C$_{2-10}$ alkynyl, C$_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally optimally substituted by one to more substituent groups; and the substituent groups are arbitrarily selected from hydrogen, deuterium, halogen, alkyl, haloalkyl, alkoxyl, alkylamino, O=, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent $R_1$ or any two adjacent $R_2$ form 5-6 membered aryl or heteroaryl, 3-8 membered saturated or partially saturated cycloalkyl, and 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, $CF_3$, OH, $OCH_3$, and $OCH_2CH_3$;

heteroatoms in the heteroaryl and heterocyclyl represent any heteroatom independently selected from O, N, S, and P, and isotopes thereof;

the halogen is arbitrarily independently selected from F, Cl, Br, and I, and isotopes thereof; and m is an integer arbitrarily selected from 0, 1, 2, 3 and 4; and n is an integer arbitrarily selected from 0, 1, 2, 3 and 4.

In a scheme of the present invention, the quaternary ammonium salt conjugated compound or the pharmaceutically acceptable salt, the solvate, the enantiomer and the isotope substitution, the composition or the double salt thereof has a structure as represented by formula (IB),

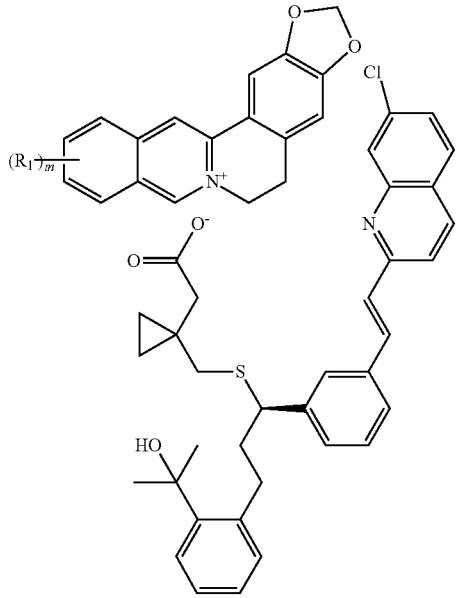

formula (IB)

wherein
$R_1$ is independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally optimally substituted by one to more substituent groups; and the substituent groups are arbitrarily selected from hydrogen, deuterium, halogen, alkyl, haloalkyl, alkoxyl, alkylamino, O=, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent $R_1$ form 5-6 membered aryl or heteroaryl, 3-8 membered saturated or partially saturated cycloalkyl, and 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, $CF_3$, OH, $OCH_3$, and $OCH_2CH_3$;

heteroatoms in the heteroaryl and heterocyclyl represent any heteroatom independently selected from O, N, S, and P, and isotopes thereof;

the halogen is arbitrarily independently selected from F, Cl, Br, and I, and isotopes thereof; and m is an integer arbitrarily selected from 0, 1, 2, 3 and 4.

In a scheme of the present invention, the quaternary ammonium salt conjugated compound or the pharmaceutically acceptable salt, the solvate, the enantiomer and the isotope substitution, the composition or the double salt thereof has a structure as represented by formula (IC),

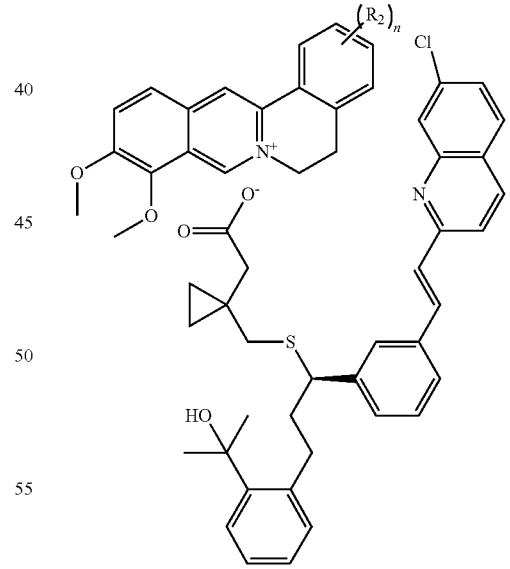

formula (IC)

wherein
$R_2$ is independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally optimally substituted by one to more substituent groups; and the substituent groups are arbitrarily selected from hydrogen, deuterium, halogen, alkyl, haloalkyl, alkoxyl, alkylamino, O=, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent $R_2$ form 5-6 membered aryl or heteroaryl, 3-8 membered saturated or partially saturated cycloalkyl, and 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, $CF_3$, OH, $OCH_3$, and $OCH_2CH_3$;

heteroatoms in the heteroaryl and heterocyclyl represent any heteroatom independently selected from O, N, S, and P, and isotopes thereof;

the halogen is arbitrarily independently selected from F, Cl, Br, and I, and isotopes thereof; and n is an integer arbitrarily selected from 0, 1, 2, 3 and 4.

In a scheme of the present invention, the quaternary ammonium salt conjugated compound or the pharmaceutically acceptable salt, the solvate, the enantiomer and the isotope substitution, the composition or the double salt thereof has a structure as represented by formula (ID)

formula (ID)

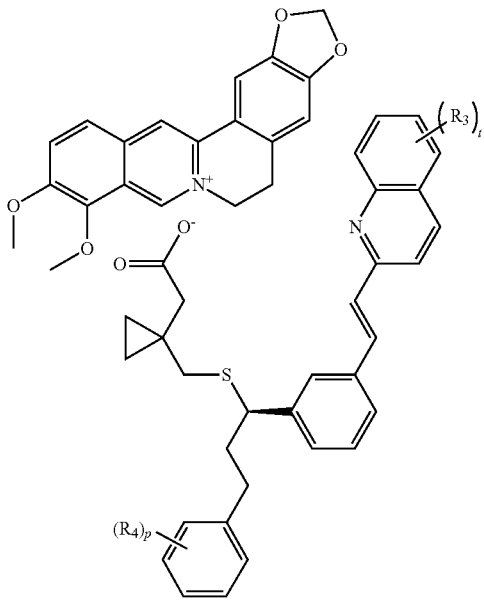

wherein
$R_3$ and $R_4$ are independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally optimally substituted by one to more substituent groups; and the substituent groups are arbitrarily selected from hydrogen, deuterium, halogen, alkyl, haloalkyl, alkoxyl, alkylamino, O=, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent $R_3$ or any two adjacent $R_4$ form 5-6 membered aryl or heteroaryl, 3-8 membered saturated or partially saturated cycloalkyl, and 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, $CF_3$, OH, $OCH_3$, and $OCH_2CH_3$;

heteroatoms in the heteroaryl and heterocyclyl represent any heteroatom independently selected from O, N, S, and P, and isotopes thereof;

the halogen is arbitrarily independently selected from F, Cl, Br, and I, and isotopes thereof; and P is an integer arbitrarily selected from 0, 1, 2, 3, 4 and 5; and t is an integer arbitrarily selected from 0, 1, 2, 3, 4 and 5.

According to an embodiment of the present invention, each $R_1$ is the same or different, and is each independently selected from hydrogen, $C_{1-6}$ alkyl, and $C_{1-6}$ alkoxyl; or two $R_1$ form a 3-8 membered heterocyclic ring together with carbons respectively connected thereto.

According to an embodiment of the present invention, each $R_1$ is the same or different, and is each independently selected from hydrogen, methyl or methoxyl; or two $R_1$ form

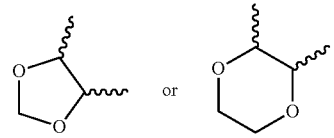

together with carbons respectively connected thereto.

According to an embodiment of the present invention, each $R_2$ is the same or different, and is each independently selected from hydrogen, $C_{1-6}$ alkyl, and $C_{1-6}$ alkoxyl; or two $R_2$ form a 3-8 membered heterocyclic ring together with carbons respectively connected thereto.

According to an embodiment of the present invention, each $R_2$ is the same or different, and is each independently selected from hydrogen, methyl or methoxyl; or two $R_2$ form

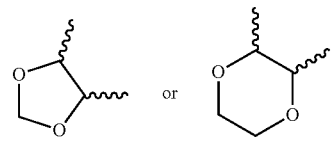

together with carbons respectively connected thereto.

According to an embodiment of the present invention, each $R_3$ is the same or different, and is each independently selected from hydrogen, hydrogen, $C_{1-6}$ alkyl, and $C_{1-6}$ alkoxyl.

According to an embodiment of the present invention, each $R_3$ is the same or different, and is each independently selected from fluorine, chlorine, bromine or iodine, preferably chlorine.

According to an embodiment of the present invention, each $R_4$ is the same or different, and is each independently selected from hydrogen or hydroxy $C_{1-6}$ alkyl.

According to an embodiment of the present invention, $R_4$ is selected from hydrogen or Compound 1

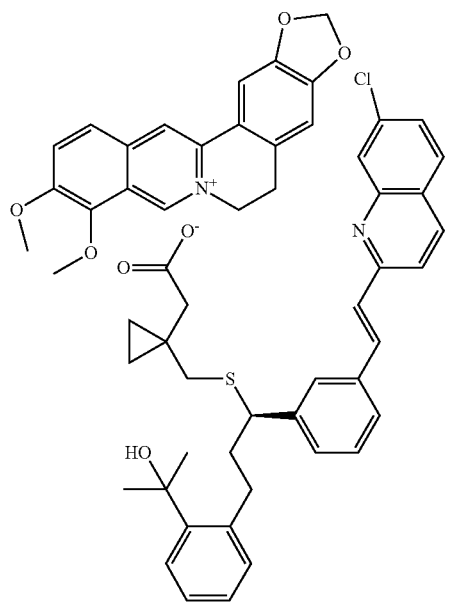

Compound 2

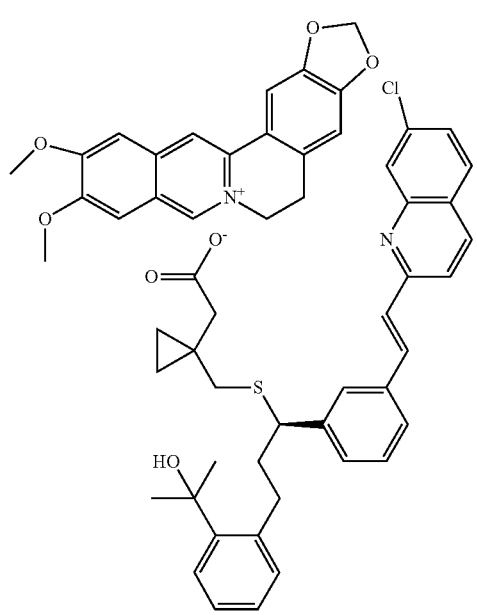

Compound 3

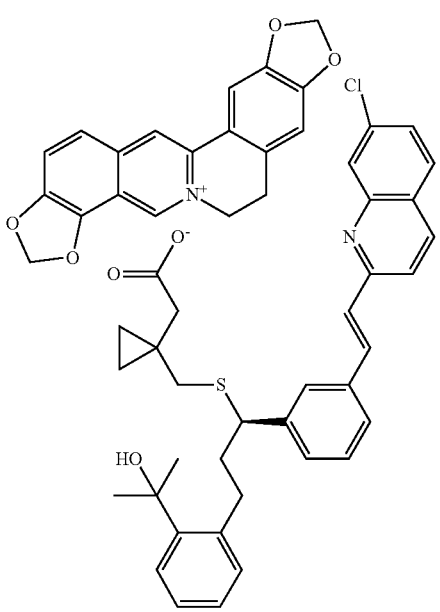

Compound 4

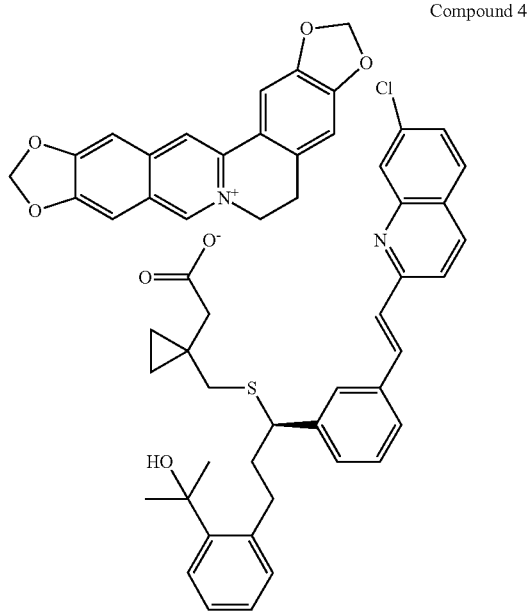 [SMILES: c1c2c(cc3c1OCO3)-c1cc3cc4c(cc3c[n+]1CC2)OCO4 ; CC(C)(O)c1ccccc1CC[C@@H](SCC1(CC(=O)[O-])CC1)c1cccc(/C=C/c2ccc3ccc(Cl)cc3n2)c1]

According to an embodiment of the present invention, m is selected from 0, 1, 2 or 3.

According to an embodiment of the present invention, n is selected from 0, 1, 2 or 3.

According to an embodiment of the present invention, t is selected from 0 or 1.

According to an embodiment of the present invention, p is selected from 0 or 1.

In some schemes of the present invention, the quaternary ammonium salt conjugated compound or the pharmaceutically acceptable salt, the solvate, the enantiomer and the isotope substitution, the composition or the double salt thereof is selected from the following structures:

Compound 1
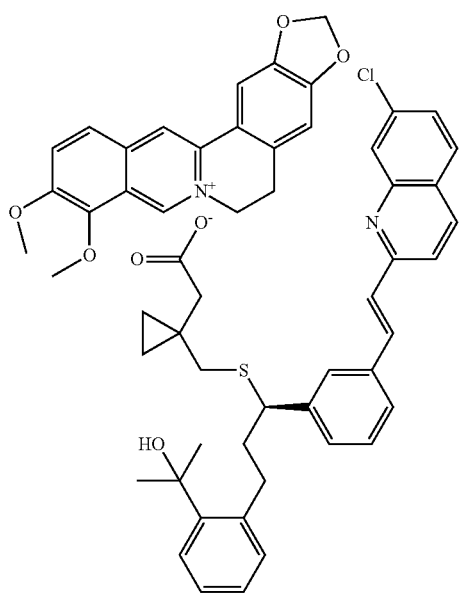
Compound 2
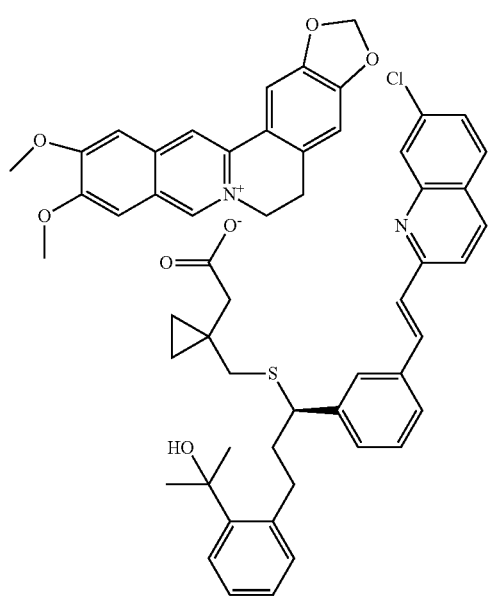
Compound 3
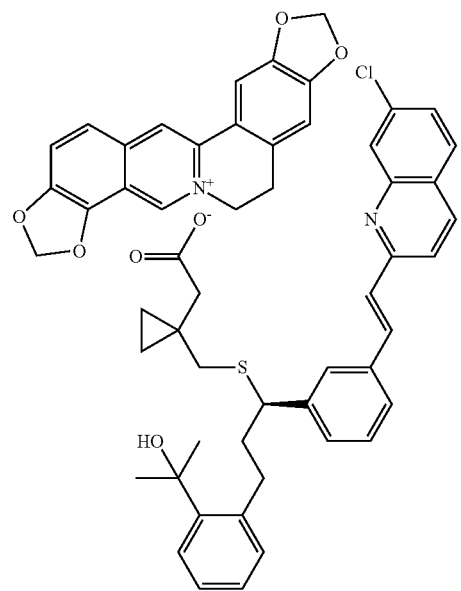
Compound 4
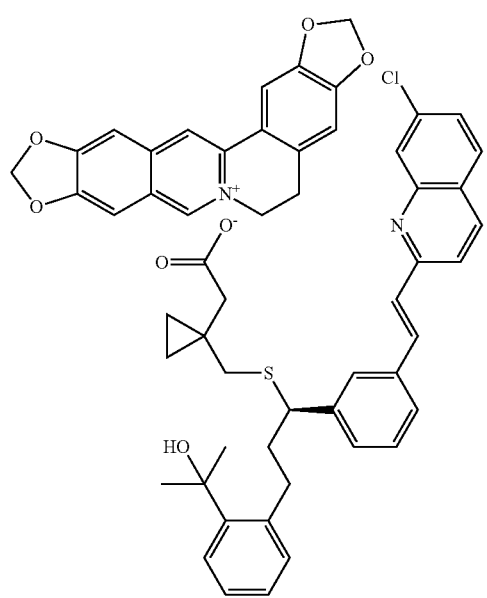

Compound 5
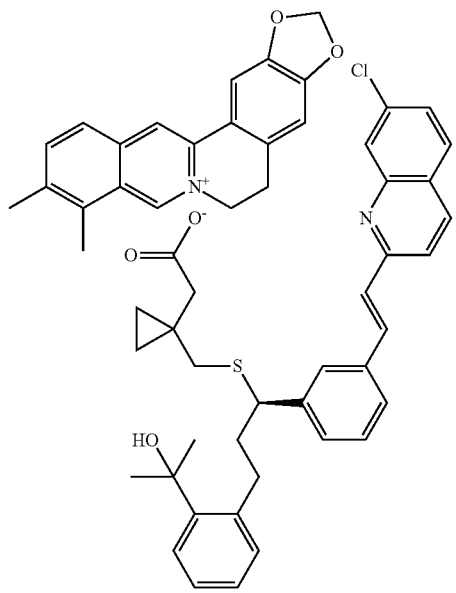
Compound 7
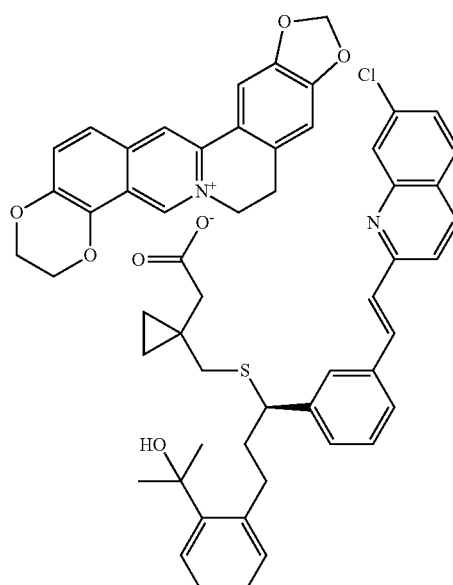
Compound 6
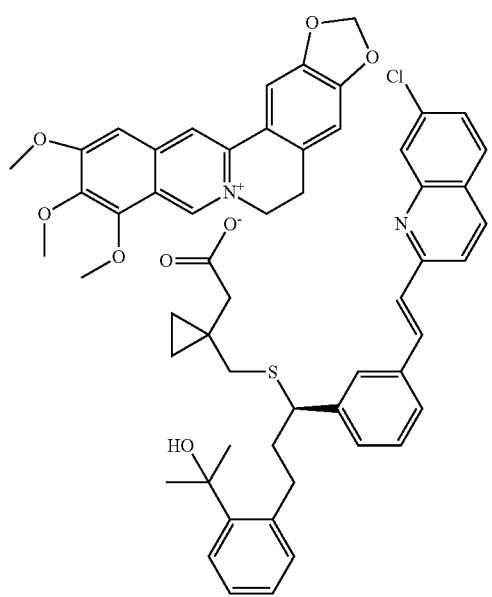
Compound 8
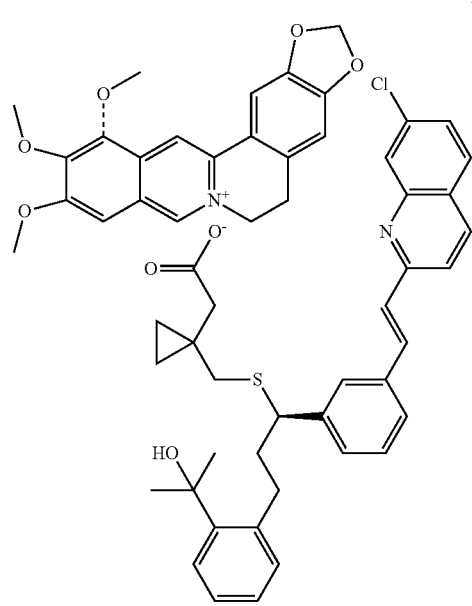

Compound 9
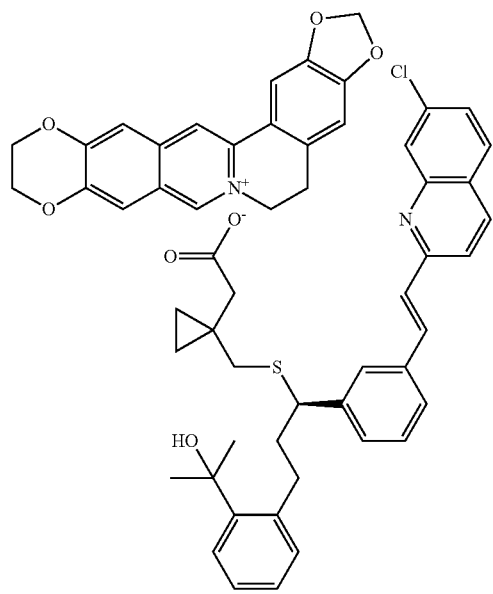
Compound 10
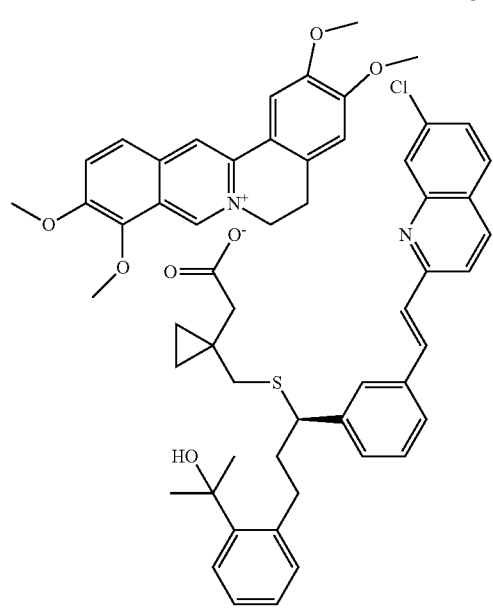
Compound 11
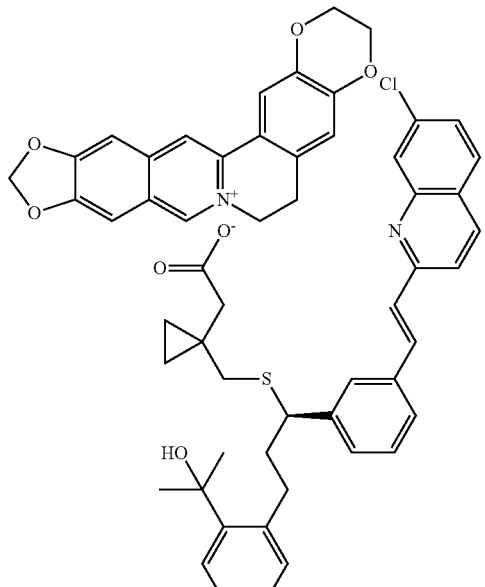
Compound 12
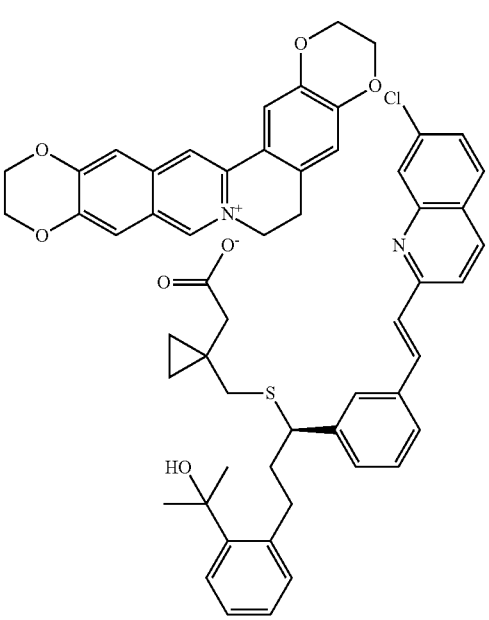

-continued

Compound 13

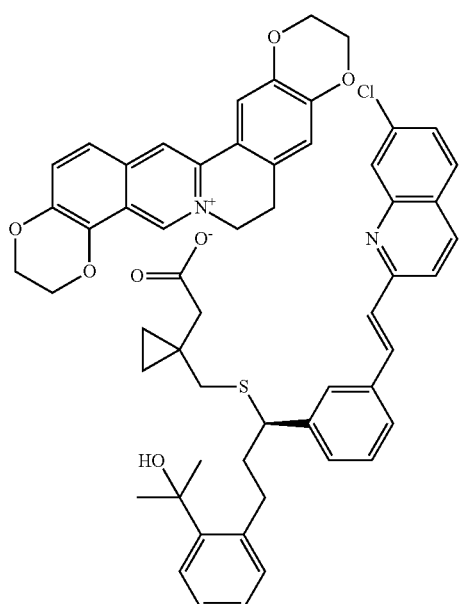

Compound 14

-continued

Compound 15

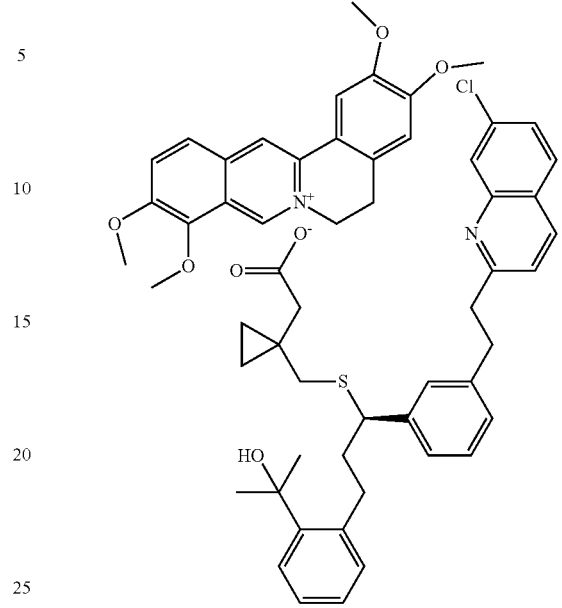

Another object of the present invention is to provide a synthesis method for the quaternary ammonium salt conjugated compound, the solvate, the enantiomer, the isotope substitution and the double salt composition includes the following steps:

1) preparation of various free berberine alkaloid acetone addition products: weighing berberine alkaloid quaternary ammonium salt compounds of various acid radicals on demand and placing in a reaction flask, adding an inorganic base (usually sodium hydroxide or KOH aqueous solution), then adding acetone dropwise, and stirring for reaction until the raw materials are completely reacted; performing suction filtration on the reaction mixture, washing a filter cake with water until neutral, and drying to obtain various free berberine alkaloid acetone addition products; and 2) preparation of the quaternary ammonium salt conjugated compound, solvate or composition: weighing montelukast on demand and placing in a reaction flask, adding ethyl acetate to dissolve fully, and then adding an 8-acetonyl dihydroberberine alkaloid compound for reaction under stirring until the raw materials are completely reacted, followed by concentration under reduced pressure or crystallization; or adding an appropriate anti-solvent to the reaction mixture to obtain a berberine montelukast double salt composition.

Another object of the present invention is to provide applications of the compound as represented by formula (I) or the pharmaceutically acceptable salt, the solvate, the composition, the enantiomer and the isotope substitution or the double salt thereof in the preparation of drugs for prevention, alleviation and/or treatment of diseases related to allergy, inflammations, vascular malformation, infections, immunity and others, such as ulcerative colitis, rhinitis, asthma, vascular malformation/vasculitis, dry eye and eye infections.

According to an embodiment of the present invention, the diseases to be prevented or treated include, but are not limited to, overweight, obesity, diabetes (T1 D and/or T2DM, including prediabetes), idiopathic T1 D (type 1B), latent autoimmune diabetes in adults (LADA), early-onset T2DM (EOD), young-onset atypical diabetes (YOAD), maturity-onset diabetes of the young (MODY), malnutrition-related diabetes, gestational diabetes, hyperglycemia, insulin resistance, hepatic insulin resistance, impaired glucose tolerance, diabetic neuropathy, diabetic nephropathy, renal diseases (e.g., acute kidney diseases, renal tubular dysfunction, and proinflammatory changes in proximal tubules), diabetic retinopathy, adipocyte dysfunction, visceral fat deposition, sleep apnea, obesity (including hypothalamic obesity and monogenic obesity), as well as related comorbidities (e.g., osteoarthritis and urinary incontinence), drinking and eating disorders (including binge eating syndromes, bulimia nervosa and syndromic obesity, such as Prader-Willi and Bardet-Biedl syndromes), weight gain from use of other drugs (e.g., use of steroids and antipsychotics), addicted to sugar, dyslipidemia (including hyperlipidemia, hypertriglyceridemia, total cholesterol increase, high-density lipoprotein cholesterol, low-density lipoprotein cholesterol, hyperinsulinemia, NAFLD (including steatosis, NASH, fibrosis, liver cirrhosis, hepatocellular carcinoma and other related diseases), cardiovascular diseases, atherosclerosis (including coronary artery diseases), peripheral vascular diseases, hypertension, endothelial dysfunction, impaired vascular compliance, congestive heart failure, myocardial infarction (e.g., necrosis and apoptosis), stroke, hemorrhagic stroke, ischemic stroke, traumatic brain injury, pulmonary hypertension, restenosis after angioplasty, intermittent claudication, postprandial hyperlipidemia, metabolic acidosis, ketosis, arthritis, osteoporosis, Parkinson's disease, left ventricular hypertrophy, peripheral arterial disease, macular degeneration, cataract, dry eye, glomerulosclerosis, chronic renal failure, metabolic syndrome, syndrome X, premenstrual syndrome, angina, thrombosis, atherosclerosis, transient ischemic attack, vascular restenosis, impaired glucose metabolism, impaired fasting glucose, hyperuricemia, gout, erectile dysfunction, skin and connective tissue diseases, psoriasis, foot ulcers, ulcerative colitis, hyperapolipoprotein B lipoproteinemia, Alzheimer's disease, schizophrenia, cognitive impairment, inflammatory bowel disease, short bowel syndrome, Crohn's disease, colitis, irritable bowel syndrome, and polycystic ovary syndrome, as well as diseases related to addiction treatment such as alcoholism and/or drug abuse.

The present invention further provides a pharmaceutical composition, which contains a therapeutically effective amount of at least one of the compound as represented by formula (I) or the pharmaceutically acceptable salt, the solvate, the composition, the enantiomer and the isotope substitution or the double salt thereof or a pharmaceutically acceptable carrier or excipient.

According to an embodiment of the present invention, the pharmaceutical composition is prepared for administration by a route selected from the group consisting of: oral, injectable, rectal, nasal, pulmonary, topical, buccal and sublingual, vaginal, parenteral, subcutaneous, intramuscular, intravenous, intradermal, intrathecal, and epidural.

According to an embodiment of the present invention, the pharmaceutical composition is preferably administered orally.

The oral dosage form is not particularly limited, and any oral dosage form known in the art may be used, preferably including tablets, capsules, suspensions, oral solutions and other oral dosage forms known in the art. As an oral dosage form, a dosage standard used is, for example, 500-1500 mg/day, preferably 700-1200 mg/day, preferably 800-1000 mg/day, most preferably 1000 mg/day.

A medication time of the pharmaceutical composition according to the present invention may be determined according to the severity of a disease, preferably at least 1 month, for example, 1, 2, 3, 4, 5 or 6 months, with a possible maximum to lifelong medication due to the needs of the disease.

According to an embodiment of the present invention, the pharmaceutical composition may further include a pharmaceutically acceptable adjuvant, which is selected from at least one of the following adjuvants, including but not limited to: a filler, a disintegrant, a binder, a lubricant, a surfactant, a flavoring agent, a wetting agent, a pH regulator, a solubilizer or a co-solvent, or an osmotic pressure regulator. Those skilled in the art may easily determine how to select the corresponding adjuvants and their corresponding dosages according to the needs of specific dosage forms.

According to an embodiment of the present invention, the pharmaceutical composition may further contain one or more additional therapeutic agents.

Another object of the present invention is to provide a berberine montelukast double salt composition, wherein the berberine montelukast double salt composition is prepared into a clinically acceptable pharmaceutical preparation by taking the berberine montelukast double salt as an effective ingredient and adding appropriate adjuvants and carriers.

The present invention further provides uses of the compound as represented by formula (I) or the pharmaceutically acceptable salt, the solvate, the composition, the enantiomer and the isotope substitution or the double salt thereof, and the pharmaceutical composition in the prevention or treatment of diseases related to inflammations, immunity, infection, allergy, metabolism and others. The diseases related to inflammations, immunity, infection, allergy, metabolism and others have the above-mentioned definitions.

The present invention further provides a method for prevention or treatment of diseases related to inflammation, immunity, infection, allergy, metabolism and others, including: administering a patient with a preventively or therapeutically effective amount of at least one of the compound as represented by formula (I) or the therapeutically acceptable salt, the solvate, the composition, the enantiomer and the isotope substitution or the double salt thereof; or administrating a patient with a preventively or therapeutically effective amount of the pharmaceutical composition. The diseases related to inflammations, immunity, infection, allergy, metabolism and others have the above-mentioned definitions.

In some embodiments, the patient is a mammal, preferably a human.

The present invention is now further described by examples. The following examples are only used for an illustrative purpose, but not to limit the scope of the present invention. The compound of the present invention may be prepared by many known methods in the field of organic synthesis. The examples of the present invention may be synthesized using the method described below, as well as a synthesis method known in the field of organic synthetic chemistry, or by an improved method on its basis. Preferred methods include, but are not limited to, the methods described below.

The compound may be named manually, or may be named by ChemDraw®, or may use a supplier catalog name if purchased commercially.

DETAILED DESCRIPTION OF THE INVENTION

Figure 1:
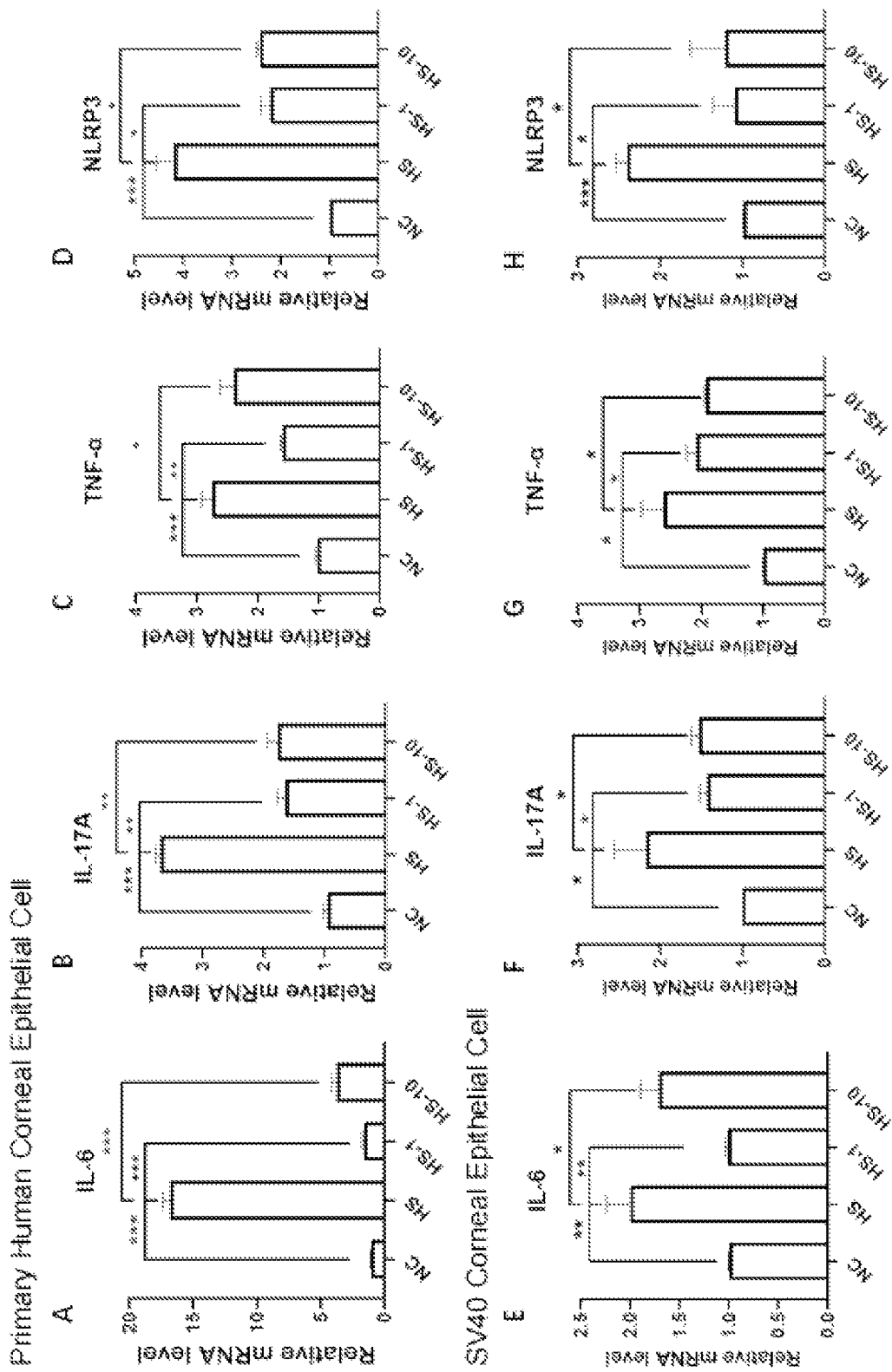
FIG. 1 is a comparison diagram of anti-inflammatory effects of different concentrations of double salt compounds in Example 3.
Figure 2:
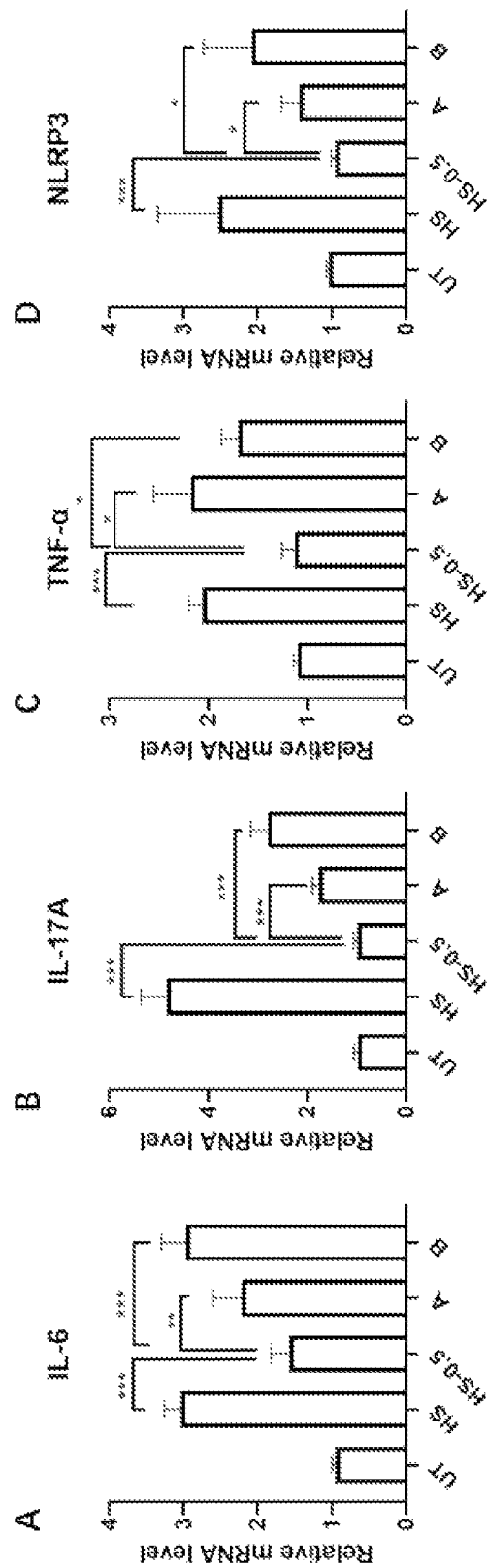
FIG. 2 is a comparison diagram of anti-inflammatory effects of double salts and monomers thereof in Example 4.

In order to illustrate the present invention in more detail, the following examples are given, but the scope of the present invention is not limited thereto.

Example 1: Preparation of Montelukast Berberine Double Salt (Double Salt 1)

1. Synthesis of 1-(9,10-dimethoxy-5,8-dihydro-6H-[1,3]dioxacyclo[4,5-g]isoquinolinyl[3,2-a]isoquinolin-8-yl) propan-2-one

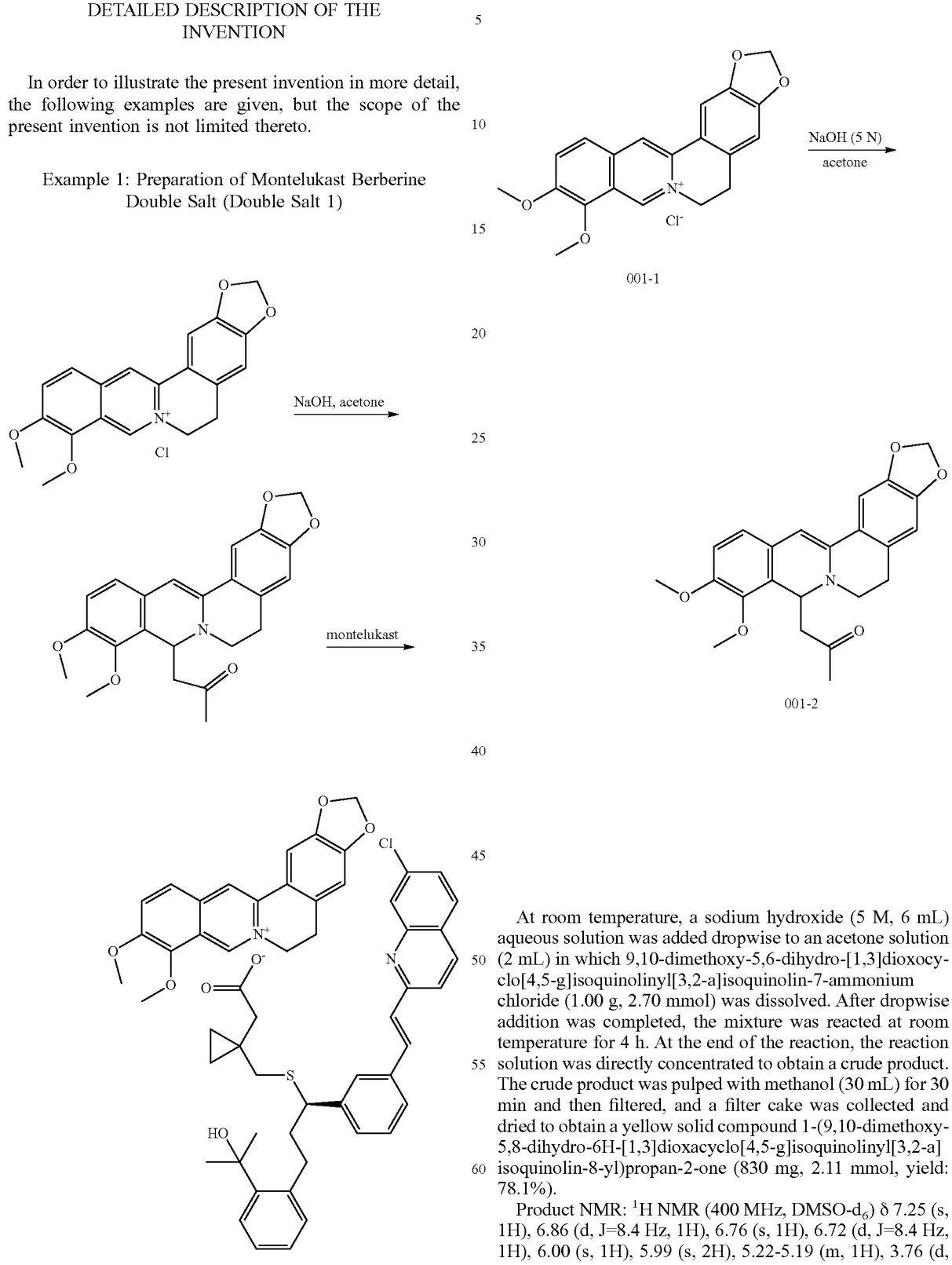

At room temperature, a sodium hydroxide (5 M, 6 mL) aqueous solution was added dropwise to an acetone solution (2 mL) in which 9,10-dimethoxy-5,6-dihydro-[1,3]dioxocyclo[4,5-g]isoquinolinyl[3,2-a]isoquinolin-7-ammonium chloride (1.00 g, 2.70 mmol) was dissolved. After dropwise addition was completed, the mixture was reacted at room temperature for 4 h. At the end of the reaction, the reaction solution was directly concentrated to obtain a crude product. The crude product was pulped with methanol (30 mL) for 30 min and then filtered, and a filter cake was collected and dried to obtain a yellow solid compound 1-(9,10-dimethoxy-5,8-dihydro-6H-[1,3]dioxacyclo[4,5-g]isoquinolinyl[3,2-a]isoquinolin-8-yl)propan-2-one (830 mg, 2.11 mmol, yield: 78.1%).

Product NMR: $^1$H NMR (400 MHz, DMSO-$d_6$) δ 7.25 (s, 1H), 6.86 (d, J=8.4 Hz, 1H), 6.76 (s, 1H), 6.72 (d, J=8.4 Hz, 1H), 6.00 (s, 1H), 5.99 (s, 2H), 5.22-5.19 (m, 1H), 3.76 (d, J=2.4 Hz, 6H), 3.30-3.26 (m, 1H), 3.20-3.19 (m, 1H), 2.96-2.90 (m, 1H), 2.78-2.76 (m, 2H), 2.33-2.29 (m, 1H), 2.03 (s, 3H).

2. Synthesis of (R,E)-2-(1-(((1-(3-(2-(7-chloroquinolin-2-yl)vinyl)phenyl)-3-(2-(2-hydroxypropyl-2-yl)phenyl) propyl)thio)methyl)cyclopropyl)acetic acid and 9,10-dimethoxy-5,6-dihydro-[1,3]dioxocyclo[4,5-g]isoquino[3,2-a]isoquinolin-7-onium conjugate

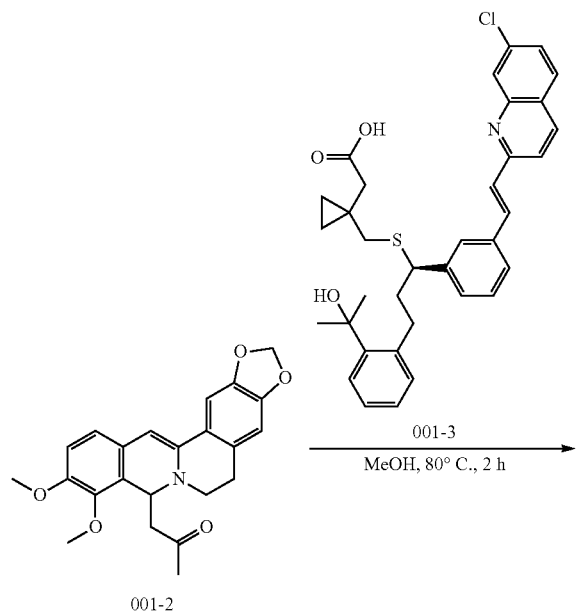

A compound 1-(9,10-dimethoxy-5,8-dihydro-6H-[1,3]dioxane[4,5-g]isoquinolinyl[3,2-a]isoquinolin-8-yl)propan-2-one (791 mg, 2.01 mmol) and a compound (R,E)-2-(1-(((1-(3-(2-(7-chloroquinoline-2-yl)vinyl)phenyl)-3-(2-(2-hydroxypropyl-2-yl)phenyl)propyl)thio)methyl)cyclopropyl)acetic acid (1.18 g, 2.01 mmol) were added in a sealed tube containing methanol (8 mL) and water (0.1 mL), and then the reaction solution was heated to 80° C. and reacted for 2 h. At the end of the reaction, a solvent was removed from the reaction solution to obtain a yellow solid compound (11.90 g, 2.06 mmol, crude product). Then, the crude product compound (600 mg, 0.65 mmol) was added to a mixed solvent (chloroform (6.5 mL), methanol (3.5 mL) and water (0.1 mL)), heated to 80° C. until the crude product was completely dissolved, and stirred at 80° C. for 1 h. At the end of the reaction, the reaction solution was naturally cooled to room temperature, and the reaction solution was directly concentrated to remove the solvent to obtain (R,E)-2-(1-(((1-(3-(2-(7-chloroquinoline-2-yl)vinyl)phenyl)-3-(2-(2-hydroxypropyl-2-yl)phenyl)propyl)thio)methyl)cyclopropyl)acetic acid and 9,10-dimethoxy-5,6-dihydro-[1,3]dioxocyclo [4,5-g]isoquino[3,2-a]isoquinolin-7-onium conjugate (double salt 1, 600 mg, 0.65 mmol, yield: 100%), retention time: 1.271 min. LCMS: [M+H]$^+$ 336.1. Retention time: 1.853 min. LCMS: [M+H]$^+$ 586.3.

Product NMR: $^1$H NMR (400 MHz, DMSO) δ9.89 (s, 1H), 8.93 (s, 1H), 8.40 (d, J=8.8 Hz, 1 H), 8.20 (d, J=9.2 Hz, 1H), 8.03 (d, J=12.4 Hz, 1H), 8.01-7.94 (m, 3H), 7.89 (d, J=16.4 Hz, 1H), 7.80 (s, 1H), 7.73 (s, 1H), 7.62-7.57 (m, 2H), 7.51 (d, J=116.4 Hz, 1H), 7.40-7.33 (m, 3H), 7.11-7.00 (m, 4H), 6.17 (s, 2H), 4.94-4.91 (m, 2H), 4.08 (d, J=10.0 Hz, 6H), 4.02 (t, J=8.0 Hz, 1H), 3.25-3.19 (m, 2H), 3.13-3.06 (m, 1H), 2.75-2.65 (m, 2H), 2.54 (s, 1H), 2.29-2.20 (m, 1H), 2.10-2.06 (m, 2H), 1.95-1.91 (m, 1H), 1.45 (d, J=8.4 Hz, 6H), 0.41-0.30 (m, 2H), 0.25-0.14 (m, 2H).

Montelukast

Example 2: Preparation of Montelukast Berberine Analogue Double Salts (Double Salts 2-15)

| Nos. of Compounds | Structure |
|---|---|
| Double salt 2 | 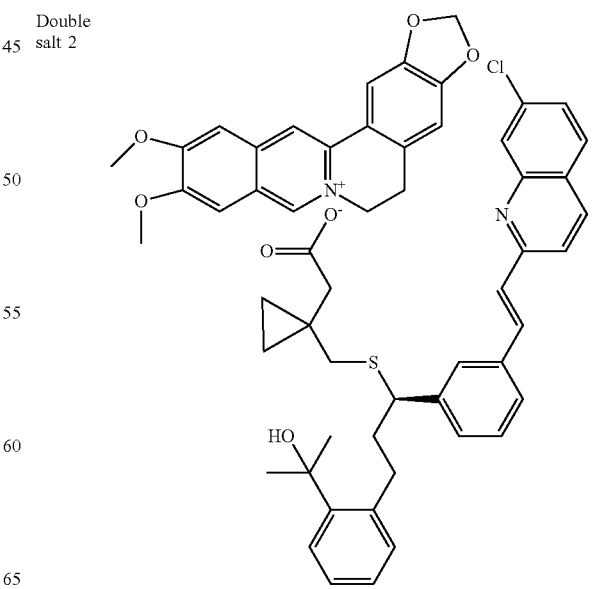 |

| Nos. of Compounds | Structure |
|---|---|
| Double salt 3 | 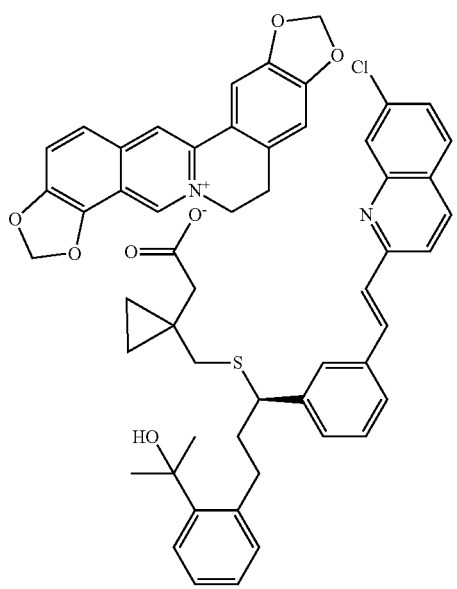 [SMILES: c1c2c(cc3c1OCO3)-c1cc3ccc4c(c3c[n+]1CC2)OCO4 ; CC(C)(O)c1ccccc1CC[C@@H](SCC1(CC(=O)[O-])CC1)c1cccc(/C=C/c2ccc3ccc(Cl)cc3n2)c1] |
| Double salt 4 | 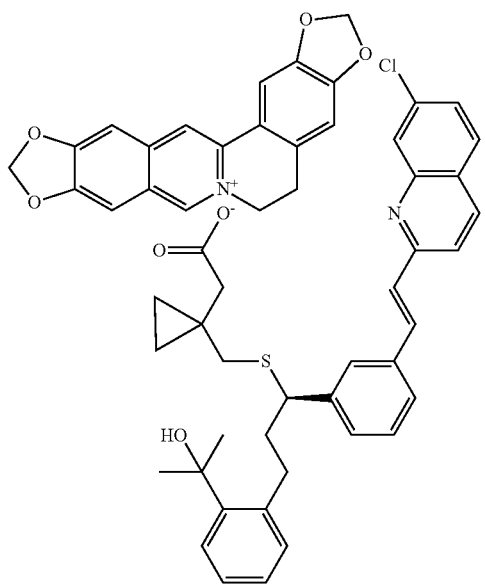 [SMILES: c1c2c(cc3c1OCO3)-c1cc3cc4c(cc3c[n+]1CC2)OCO4 ; CC(C)(O)c1ccccc1CC[C@@H](SCC1(CC(=O)[O-])CC1)c1cccc(/C=C/c2ccc3ccc(Cl)cc3n2)c1] |
| Double salt 5 | 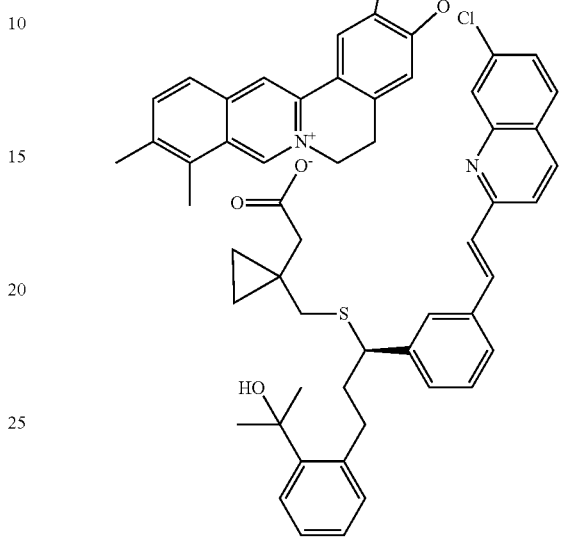 |
| Double salt 6 | 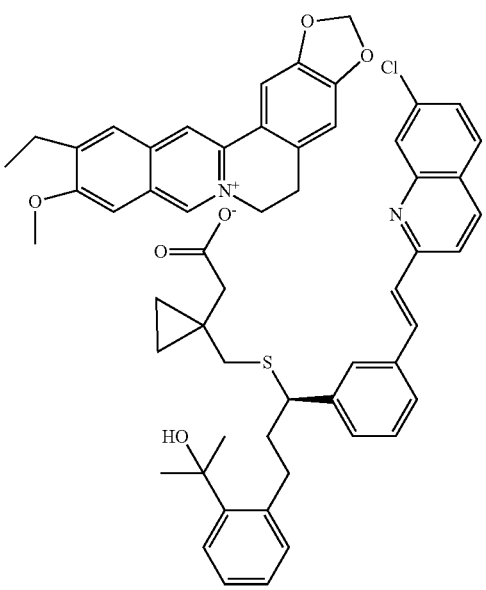 [SMILES: CCc1cc2cc3[n+](cc2cc1OC)CCc1cc2c(cc1-3)OCO2 ; CC(C)(O)c1ccccc1CC[C@@H](SCC1(CC(=O)[O-])CC1)c1cccc(/C=C/c2ccc3ccc(Cl)cc3n2)c1] |

-continued
| Nos. of Compounds | Structure |
|---|---|
| Double salt 7 | 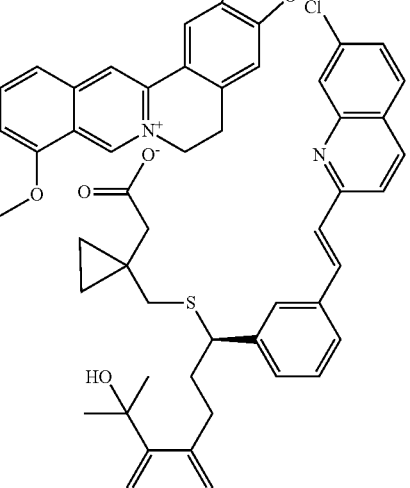 |
| Double salt 8 | 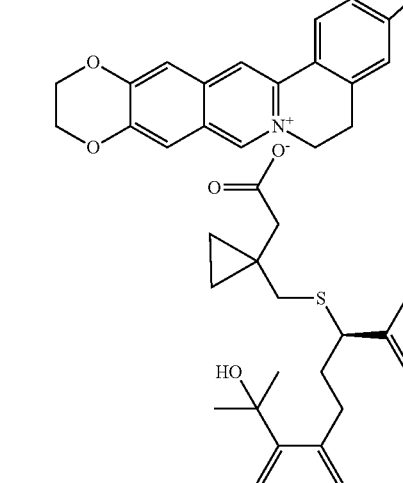 |
-continued
| Nos. of Compounds | Structure |
|---|---|
| Double salt 9 | 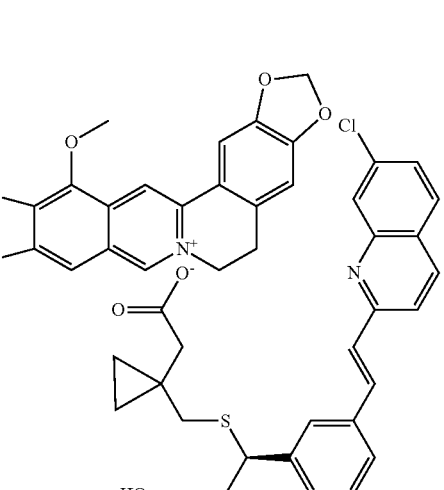 |
| Double salt 10 | 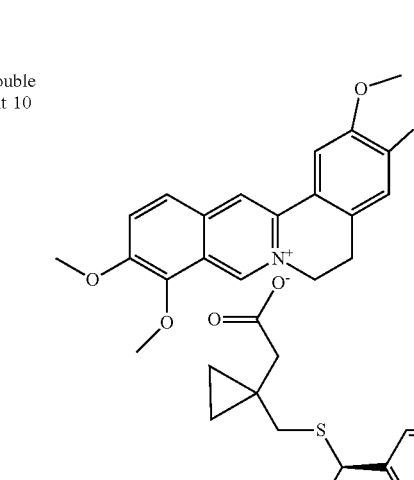 |

| Nos. of Compounds | Structure |
|---|---|
| Double salt 11 | 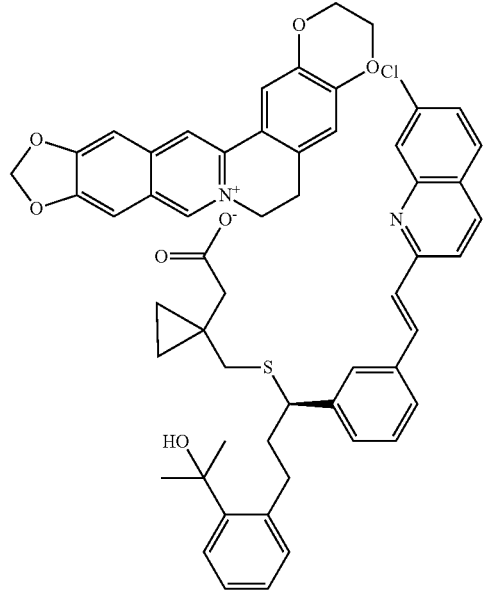 [SMILES: c1c2c(cc3c1OCCO3)-c1cc3cc4c(cc3c[n+]1CC2)OCO4 ; CC(C)(O)c1ccccc1CC[C@@H](SCC1(CC(=O)[O-])CC1)c1cccc(/C=C/c2ccc3ccc(Cl)cc3n2)c1] |
| Double salt 12 | 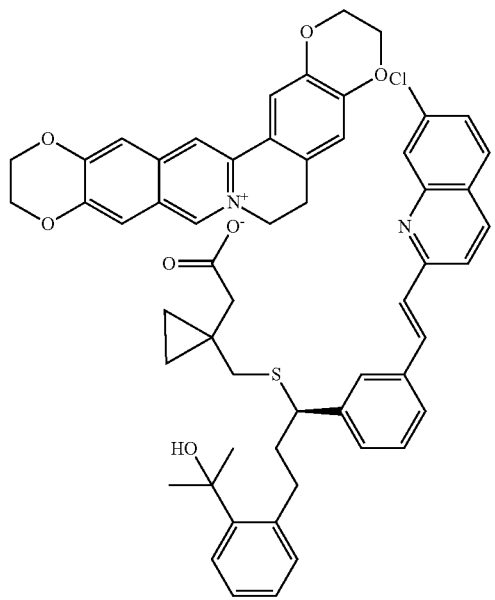 [SMILES: c1c2c(cc3c1OCCO3)-c1cc3cc4c(cc3c[n+]1CC2)OCCO4 ; CC(C)(O)c1ccccc1CC[C@@H](SCC1(CC(=O)[O-])CC1)c1cccc(/C=C/c2ccc3ccc(Cl)cc3n2)c1] |
| Nos. of Compounds | Structure |
|---|---|
| Double salt 13 | 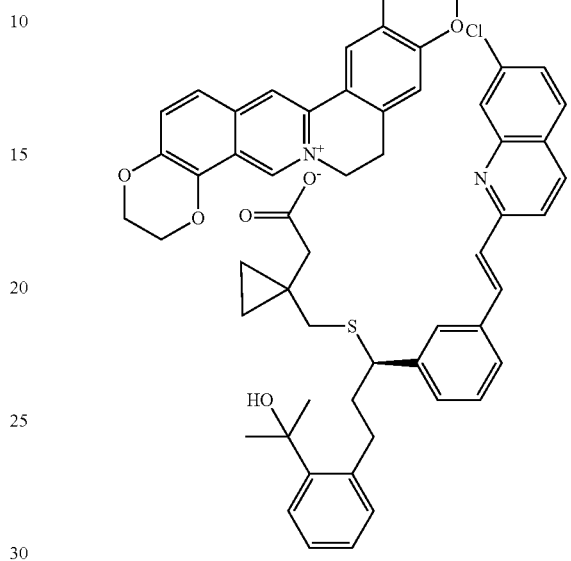 |
| Double salt 14 | |

| Nos. of Compounds | Structure |
|---|---|
| Double salt 15 | (structure diagram) |

Example 3: Evaluation on Anti-Inflammatory Effect of Test Compound Through Hypertonic Inflammatory Cell Model 3.1 Cells and Culture

| Cell line | Culture method |
|---|---|
| Human 12-SV40 corneal epithelial cell line | DMEM/F12 + 10% FBS + 1% ITS |
| Primary human corneal epithelial cell | DMEM/F12 + 5% FBS + 10 ng/ml EGF + 1% ITS + 0.5% DMSO + 0.5 μg/ml Hydrocortison + 50 μg/ml Gentamicin + 1.25 μg/ml amphotericin B |

3.2 Reagents, Instruments and Consumables

| Reagents and consumables | Manufacturers |
|---|---|
| PBS | Gibco |
| FBS | Gibco |
| DMSO | SIGMA |
| L-glutamine | Gibco |
| DMEM/F12 | Gibco |
| Human epidermal growth factor | Gibco |
| Primers | Invitrogen |
| Centrifuge tube | Falcon Inc., USA |
| Cell culture plate | Falcon Inc., USA |
| Hanks | Gibco |
| Mycillin solution (100×) | Gibco |
| Insulin, Transferrin, Selenium, Ethanolamine Solution (ITS-X), 100× | Gibco |
| 0.25% EDTA-containing trypsin | Gibco |
| NaCl powder | Sigma |
| CCK8 kit (cell counting kit-8) | DOJINDO |
| Ophthalmic scissors, ophthalmic tweezers | 66 VISION TECH |
| Hydrocortison | Solarbio |
| Gentamicin | Solarbio |
| Amphotericin B | Sigma |

3.3 Experimental Method and Process

SV40 cell culture: SV40 cells were cultured in a DMEM/F12 medium containing 10% fetal bovine serum, and added with insulin and a human epidermal growth factor at the same time, so that a final concentration of insulin in the medium was 5 μg/mL and a final concentration of the human epidermal growth factor was 10 ng/mL. The medium was routinely subcultured in a cell culture incubator with a temperature of 37° C., CO2 content of 5% and a humidity of 90%. The cells were grown to a fused state of 70%-90% for an experiment.

Primary human cell culture: the remaining limbus of the donor cornea used in a surgery was treated with an ophthalmic instrument into a tissue block carrying corneal stem cells, the tissue block was pasted at the bottom of a cell culture dish, cultured in an SHEM medium, and placed in a cell culture incubator with a temperature of 37° C., CO2 content of 5% and humidity of 90%; primary human corneal epithelial cells crawling out of the limbal stem cells can be seen after 3-5 days; and the cells were grown to a fused state of 70%-90% for an experiment.

Preparation of solution: (1) preparation of hypertonic liquid (500 mOsm): 90 mmol/L NaCl solution was added to a serum-free medium. (2) Preparation of a tested drug solution: 10 mg of the above prepared product was dissolved in 1 mL of 37° C. DMSO solution, prepared into 104 μg/mL mother liquor, and stored in a −20° C. refrigerator for later use; and the mother liquor was diluted with a serum-free medium to prepare drug solutions having final concentrations of 1 μmol/L and 10 μmol/L for an experiment.

Establishment and administration of hypertonic inflammatory cell model: the old medium was discarded, and a hypertonic medium containing 500 mOsm hypertonic liquid and a normal isotonic medium were supplemented; after four hours of cell culture, a drug group was replaced with a drug solution, and the normal isotonic medium is replaced for control groups (including a hypertonic model control and a normal cell control); and materials were sampled after four hours of continuous culture.

Real-time PCR (RT-PCR): mRNA expressions of different groups of IL-6, IL-1β, IL-17A, IL-18, TNF-α, and NLRP3 were detected using RT-PCR. SV40 and primary human corneal epithelial cells inoculated in a 12-well plate at different time points (after modeling of a hypertonic inflammatory cell model and after four hours of administration) were collected for later use. The same experiment was repeated for three times. RNA was extracted from the cells according to an instruction of an RNA extraction kit, and a total amount of RNAs required to synthesize a cDNA template was calculated based on a measured concentration. cDNA was synthesized by an M-MLV reverse transcription kit, and the cDNA obtained by reverse transcription was stored at −20° C. for subsequent PCR amplification. Gene primer sequences were as follows:

| Gene name | Serial number | Forward primers | Serial number | Reverse primers |
|---|---|---|---|---|
| NLRP3 | 1 | 5'-CGTGAGTCCCATTAAGATGGAGT-3' | 2 | 5'-CCCGACAGTGGATATAGAACAGA-3' |
| IL-6 | 3 | 5'-TGAGAGTAGTGAGGAACAAG-3' | 4 | 5'-CGCAGAATGAGATGAGTTG-3' |
| IL-17A | 5 | 5'-TGTCACTGCTACTGCTGCTGAG-3' | 6 | 5'-GGTGAGGTGGATCGGTTGTAGT-3; |
| TNF-α | 7 | 5'-CCTCTCTCTAATCAGCCCTCTG-3' | 8 | 5'-GAGGACCTGGGAGTAGATGAG-3; |
| GAPDH | 9 | 5'-ATGTTCGTCATGGGTGTGAA-3' | 10 | 5'-GGTCCTAAGCAGTTGGTGGT-3'. |

A SYBR Green fluorescent dye method was used for RT-PCR detection. A relatively quantified mRNA expression quantity of a target gene was calculated. Each group was provided with three replicate wells, and a final result was taken as an average of the three times.

A t-test was used for comparison between the two groups, and P<0.05 indicated a significant difference 3.4 Results The experimental results showed (FIG. 1: NC: normal control, HS: hypertonic model, HS-1: hypertonic model+1 μmol/L montelukast berberine double salt drug treatment group, HS-10: hypertonic model+10 μmol/L montelukast berberine double salt drug treatment group), in a hypertonic model of primary human corneal epithelial cells and SV40 corneal epithelial cells, the treatments with drugs containing montelukast having concentrations of 1 μmol/L and 10 μmol/L could significantly reduce various inflammation-related cytokines (FIG. 1: A-H, HS group vs. HS-1 and HS-10 groups, Ps<0.01). It was indicated that the montelukast berberine double salt had a good anti-inflammatory effect and thus a therapeutic potential for related diseases.

Example 4: Evaluation Comparison of Anti-Inflammatory Effects of a Test Compound and Monomers Thereof Through Hypertonic Inflammatory Cell Model 4.1 Experimental Method and Process The reagents, instruments and consumables of this example were the same as those of Example 3, and contrasts drug used were berberine base (Aladdin, B414323), and montelukast (Aladdin, M421902).

Primary human cell culture: the remaining limbus of the donor cornea used in a surgery was treated with an ophthalmic instrument into a tissue block carrying corneal stem cells, the tissue block was pasted at the bottom of a cell culture dish, cultured in an SHEM medium, and placed in a cell culture incubator with a temperature of 37° C., CO2 content of 5% and humidity of 90%; primary human corneal epithelial cells crawling out of the limbal stem cells can be seen after 3-5 days; and the cells were grown to a fused state of 70%-90% for an experiment.

Preparation of solution: (1) preparation of hypertonic liquid (500 mOsm): 90 mmol/L NaCl solution was added to a serum-free medium. (2) Preparation of a tested drug solution: 10 mg of the above prepared product was dissolved in 1 mL of 37° C. DMSO solution, prepared into 104 μg/mL mother liquor, and stored in a −20° C. refrigerator for later use; and the mother liquor was diluted with a serum-free medium to prepare a drug solution having a final concentration of 0.5 μmol/L for this experiment. (3) Preparation of a drug solution of berberine and montelukast: 10 mg of berberine or montelukast was dissolved in 1 mL of 37° C. DMSO solution, respectively prepared into 104 μg/mL mother liquor, and stored in a −20° C. refrigerator for later use; and the mother liquor was diluted with a serum-free medium to prepare a drug solution having a final concentration of 0.5 μmol/L for this experiment.

Real-time PCR (RT-PCR): mRNA expressions of different groups of IL-6, IL-1β, IL-17A, IL-18, TNF-α, and NLRP3 were detected using RT-PCR. SV40 and primary human corneal epithelial cells inoculated in a 12-well plate at different time points (after modeling of a hypertonic inflammatory cell model, and four hours after administration) were taken, and cells were collected for later use. The same experiment was repeated for three times. RNA was extracted from the cells according to an instruction of an RNA extraction kit, and a total amount of RNAs required to synthesize a cDNA template was calculated based on a measured concentration. cDNA was synthesized by an M-MLV reverse transcription kit, and the cDNA obtained by reverse transcription was stored at −20° C. for subsequent PCR amplification. A gene primer sequence was the same as that in Example 3.

A t-test was used for comparison between the two groups, and P<0.05 indicated a significant difference 4.2 Results The experimental results showed (FIG. 3: UT: normal control, HS: hypertonic cell model, HS-0.5: hypertonic cell model+0.5 μmol/L montelukast berberine double salt drug treatment group, A: hypertonic cell model+0.5 μmol/L montelukast, B: hypertonic cell model+0.5 μmol/L berberine base), in a hypertonic model of primary human corneal epithelial cells, compared with a single drug of berberine and montelukast of the same concentration, the resulting double salt drug could significantly reduce various inflammation-related cytokines (FIG. 3: A-D, HS-0.5 group vs. groups A and B, Ps<0.01). It was indicated that the anti-inflammatory effect of the montelukast berberine double salt was superior to that of a montelukast or berberine monomer.

Example 5: Stability Comparison of Montelukast Berberine Double Salt with Montelukast and Berberine Base in High Humidity Environment 5.1 Experimental Method and Process In this example, a 1/10,000 electronic balance (Sartorius, Germany) was used, and contrast drugs used were berberine base (Aladdin, B414323), and montelukast (Aladdin, M421902).

Three parts of 1 g of montelukast berberine double salt (double salt 1), three parts of 1 g of montelukast and three parts of 1 g of berberine were taken respectively, respectively placed in a flat dish, and weighed precisely; a test sample was placed in a constant humidity closed container, placed under conditions of 25° C., RH90%±5% for 10 days, and weighed precisely on Day 5 and Day 10; and weighing results were recorded. A moisture absorption gain ratio was calculated.

5.2 Results

In a high humidity environment, a moisture absorption weight gain ratio of the montelukast berberine double salt was less than that of montelukast and berberine base in a high humidity environment. The compound was stored conveniently.

| Compound | Weight gain percentage of Day 5 (%) | Weight gain percentage of Day 10 (%) |
| --- | --- | --- |
| Montelukast berberine double salt | 3.3 | 4.9 |
| Montelukast | 4.5 | 5.3 |
| Berberine base | 4.2 | 6.7 |

Example 6: Solubility Comparison of Montelukast Berberine Double Salt with Montelukast and Berberine Base in a Solvent 6.1 Experimental Method and Process Preparation of solvent: 1) dissolution of carboxymethyl cellulose CMC (MACKLIN: C889437): a 2 L beaker was taken, about 1500 mL of ultrapure water at 80° C. was measured, and carboxymethyl cellulose CMC (3.75 g, 0.25%) was added slowly while stirring with an LED overhead stirrer, stirred for about 7 h and continued to be added with other adjuvants. 2) Addition of hydroxypropyl-β-cyclodextrin HPBCD (Bidepharm: BD44359): hydroxypropyl-β-cyclodextrin HPBCD (82.5 g, 5.5%) was added slowly and stirred for about 1 h until dissolved. 3) Adjustment of a pH value: a pH value was measured before adjustment of the pH value, and then 1 mol/L NaOH solution or 1 mol/L HCl solution was added to adjust the pH value to about 7.5-8.

Preparation of a reference substance: 1) montelukast berberine salt reference solution: an appropriate amount of montelukast berberine salt was weighed precisely and placed in a measuring flask, dissolved with methanol and diluted to a desired scale. 2) Berberine base reference solution: an appropriate amount of berberine reference substance was weighed precisely and placed in a measuring flask, dissolved with methanol and diluted to a desired scale. 3) Montelukast reference substance solution: 3) a montelukast reference substance was weighed precisely and placed in a measuring flask, dissolved with DMSO and diluted to a desired scale. 4) Test solution: the montelukast berberine salt, the berberine base, and the montelukast were respectively added to a solvent to be supersaturated, and filtered, and pH was adjusted to 7.5-8 with a sodium hydroxide or hydrochloric acid solution.

Chromatographic conditions: 1) chromatographic conditions of montelukast berberine salt: a chromatographic column used was Agilent ZORBAX SB-C18 (4.6×250 mm, 5 μm); a mobile phase: 0.01 mol/L ammonium dihydrogen phosphate solution (pH was adjusted to 2.8 with phosphoric acid)-acetonitrile (75:25); a detection wavelength: 345 nm; an injection volume: 10 μL; a column temperature: 25° C.; and a flow rate: 1.0 mL/min. A test solution and a reference solution of montelukast berberine salt were measured precisely and injected into a liquid chromatograph respectively. 2) Chromatographic conditions of montelukast: a chromatographic column used was Agilent Eclipse XDB-C18 (4.6×150 mm, 5 μm); a mobile phase A: 3.85 g of ammonium acetate was weighed and dissolved with 1000 mL of water, added with 1 mL of triethylamine, adjusted for a pH value to 5.5 with glacial acetic acid, filtered, and ultrasonically treated; a mobile phase B: methanol; a detection wavelength: 240 nm; an injection volume: 20 μL; a column temperature: 25° C.; and a flow rate: 1.0 mL/min. Determination method: a montelukast reference solution was measured precisely and injected into a liquid chromatograph; and various test solutions of montelukast were appropriately diluted and injected into the liquid chromatograph. 3) Chromatographic conditions of berberine base: a chromatographic column used was Agilent ZORBAX SB-C18 (4.6×250 mm, 5 μm); a mobile phase: 0.01 mol/L ammonium dihydrogen phosphate solution (pH was adjusted to 2.8 with phosphoric acid)-acetonitrile (75:25); a detection wavelength: 345 nm; an injection volume: 10 μL; a column temperature: 25° C.; and a flow rate: 1.0 mL/min. A test solution and a reference solution of berberine base were measured precisely and injected into a liquid chromatograph respectively.

A t-test was used for comparison between the two groups, and P<0.05 indicated a significant difference 6.2 Results

| Compound | Concentration in solvent (μg/ml) |
| --- | --- |
| Montelukast berberine double salt | 31.51 |
| Montelukast | Not detected for very small amount |
| Berberine base | 24.45 |

The results showed that the solubility of the montelukast berberine double salt in this solvent was superior that of the berberine base, and significantly superior to that of montelukast monomer (Ps<0.05).

Example 7: Stability Comparison of Montelukast Berberine Double Salt with Montelukast and Berberine Base in the Solvent 7.1 Experimental Method and Process The reagents, instruments and consumables in this example were the same as those of Example 6, because the solubility of montelukast in the solvent was extremely poor, so montelukast was not be detected out. Therefore, the stability of the montelukast in the solvent was compared by using a sodium salt (Aladdin: M129586) and the montelukast berberine double salt.

Preparation of solvent: 1) dissolution of carboxymethyl cellulose CMC (MACKLIN: C889437): a 2 L beaker was taken, about 1500 mL of ultrapure water at 80° C. was measured, and carboxymethyl cellulose CMC (3.75 g, 0.25%) was added slowly while stirring with an LED overhead stirrer, stirred for about 7 h and continued to be added with other adjuvants. 2) Addition of hydroxypropyl-β-cyclodextrin HPBCD (Bidepharm: BD44359): hydroxypropyl-β-cyclodextrin HPBCD (82.5 g, 5.5%) was added slowly and stirred for about 1 h until dissolved. 3) Adjustment of a pH value: a pH value was measured before adjustment of the pH value, and then 1 mol/L NaOH solution or 1 mol/L HCl solution was added to adjust the pH value to about 7.5-8.

Preparation of a reference substance: 1) montelukast berberine salt reference solution: an appropriate amount of montelukast berberine salt was weighed precisely and placed in a measuring flask, dissolved with methanol and diluted to a desired scale. 2) Berberine base reference solution: an appropriate amount of berberine reference substance was weighed precisely and placed in a measuring flask, dissolved with methanol and diluted to a desired scale. 3) Montelukast sodium reference substance solution: an appropriate amount of montelukast sodium reference substance was weighed precisely and placed in a measuring flask, dissolved with DMSO and diluted to a desired scale. 4) Test solution: the montelukast berberine salt, the berberine base, and montelukast sodium were respectively added to a solvent to be supersaturated, and filtered, and pH was adjusted to 7.5-8 with a sodium hydroxide or hydrochloric acid solution.

Chromatographic conditions: 1) chromatographic conditions of montelukast berberine salt: a column used was Agilent ZORBAX SB-C18 (4.6×250 mm, 5 μm); a mobile phase: 0.01 mol/L ammonium dihydrogen phosphate solution (pH was adjusted to 2.8 with phosphoric acid)-acetonitrile (75:25); a detection wavelength: 345 nm; an injection volume: 10 μL; a column temperature: 25° C.; and a flow rate: 1.0 mL/min. A test solution and a reference solution of montelukast berberine salt were measured precisely and injected into a liquid chromatograph respectively. 2) Chromatographic conditions of montelukast sodium: a chromatographic column used was Agilent Eclipse XDB-C18 (4.6×150 mm, 5 μm); a mobile phase A: 3.85 g of ammonium acetate was weighed and dissolved with 1000 mL of water, added with 1 mL of triethylamine, adjusted for a pH value to 5.5 with glacial acetic acid, filtered, and ultrasonically treated; a mobile phase B: methanol; a detection wavelength: 240 nm; an injection volume: 20 μL; a column temperature: 25° C.; and a flow rate: 1.0 mL/min. Determination method: a montelukast sodium reference solution was measured precisely and injected into a liquid chromatograph; and various test product solutions of montelukast sodium were appropriately diluted and injected into the liquid chromatograph. Chromatographic conditions of berberine base: a chromatographic column used was Agilent ZORBAX SB-C18 (4.6×250 mm, 5 μm); a mobile phase: 0.01 mol/L ammonium dihydrogen phosphate solution (pH was adjusted to 2.8 with phosphoric acid)-acetonitrile (75:25); a detection wavelength: 345 nm; an injection volume: 10 μL; a column temperature: 25° C.; and a flow rate: 1.0 mL/min. A test solution and a reference solution of berberine base were measured precisely and injected into a liquid chromatograph respectively.

Experimental process: 1) photostability experiment: a test solution of montelukast berberine salt at 0 h, a test solution of berberine base at 0 h, and a test solution of montelukast at 0 h were taken respectively, and the above solutions were placed under an illumination condition; samples were taken at 8 h, Day 5 and Day 10 respectively; and test solutions of various substances under various conditions were obtained and compared with a standard solution. 2) Photostability experiment: a test solution of montelukast berberine salt at 0 h, a test solution of berberine base at 0 h, and a test solution of montelukast at 0 h were taken respectively, and the above solutions were placed under conditions of 40° C. (in dark place) and 60° C. (in dark place); samples were taken at 8 h, Day 5 and Day 10 respectively; and test solutions of various substances under various conditions were obtained and compared with a standard solution.

A t-test was used for comparison between the two groups, and P<0.05 indicated a significant difference.

7.2 Results

|  |  | C(μg/ml) | Purity |  |  |  |
|---|---|---|---|---|---|---|
| Montelukast berberine salt | 0:00 | 31.51 | 94.53% |  |  |  |

|  |  | Illumination |  | 40° C. |  | 60° C. |  |
|---|---|---|---|---|---|---|---|
|  |  | C(μg/ml) | Purity | C(μg/ml) | Purity | C(μg/ml) | Purity |
|  | 8:00 | 24.68 | 92.80% | 26.8 | 94.22% | 28.81 | 93.01% |
|  | Day 5 | 15.17 | 85.74% | 26.57 | 93.19% | 28.41 | 93.00% |
|  | Day 10 | 9.75 | 79.56% | 12.27 | 92.68% | 13.70 | 92.90% |

|  |  | C(μg/ml) | Purity |  |  |  |
|---|---|---|---|---|---|---|
| Berberine base | 0:00 | 24.45 | 97.35% |  |  |  |

|  |  | Illumination |  | 40° C. |  | 60° C. |  |
|---|---|---|---|---|---|---|---|
|  |  | C(μg/ml) | Purity | C(μg/ml) | C(μg/ml) | Purity | C(μg/ml) |
|  | 8:00 | 21.84 | 97.62% | 22.62 | 97.17% | 22.45 | 97.17% |
|  | Day 5 | 14.70 | 88.52% | 22.41 | 97.02% | 21.31 | 96.96% |
|  | Day 10 | 7.02 | 74.89% | 10.35 | 96.86% | 9.68 | 95.99% |

|  |  | C(μg/ml) | Purity |
|---|---|---|---|
| Montelukast sodium | 0:00 | 3706.643 | 98.33% |

-continued

| | Illumination | | 40° C. | | 60° C. | |
|---|---|---|---|---|---|---|
| | C(μg/ml) | Purity | C(μg/ml) | C(μg/ml) | Purity | C(μg/ml) |
| 8:00 | 1444.936 | 62.47% | 3587.359 | 97.77% | 3448.598 | 96.72% |
| Day 5 | 126.667 | 23.07% | 1388.78 | 94.61% | 534.2 | 86.43% |
| Day 10 | 51.213 | 20.11% | 724.31 | 77.10% | 215.12 | 68.13% |

The results showed that the overall photothermal stability of the montelukast berberine double salt in this solvent of common eye drops at three time points of 8 h, Day 5 and Day 10 was superior to that of montelukast (Ps<0.05), and the photothermal stability was equivalent to that of the berberine base (Ps>0.05).

Embodiments of the present invention will be described above. However, the present invention is not limited to the above embodiments. Thus, any modification, equivalent replacement, improvement and so on made within the spirit and principle of the present invention shall be encompassed by the protection scope of the present invention.

What is claimed is:

1. A quaternary ammonium salt conjugated compound as represented by formula (I) or a pharmaceutically acceptable salt, a solvate, a composition, an enantiomer and an isotope substitution or a double salt thereof,

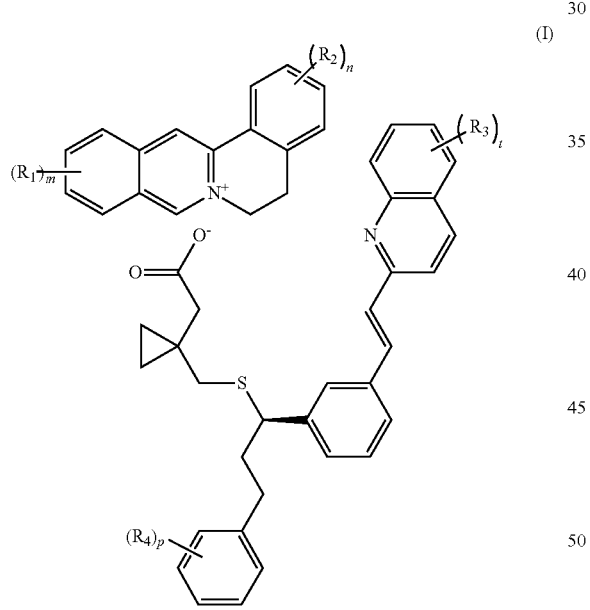

(I)

wherein $R_1$ and $R_2$ are independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally substituted by one to more substituent groups; and the substituent groups are arbitrarily selected from hydrogen, deuterium, halogen, alkyl, haloalkyl, alkoxyl, alkylamino, O═, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent $R_1$ or any two adjacent $R_2$ form 5-6 membered aryl or heteroaryl, 3-8 membered saturated or partially saturated cycloalkyl, and 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, $CF_3$, OH, $OCH_3$, and $OCH_2CH_3$;

$R_3$ and $R_4$ are independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally substituted by one to more substituent groups; and the substituent groups are arbitrarily selected from hydrogen, deuterium, halogen, alkyl, haloalkyl, alkoxyl, alkylamino, O═, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent $R_3$ or any two adjacent $R_4$ form 5-6 membered aryl or heteroaryl, 3-8 membered saturated or partially saturated cycloalkyl, and 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, $CF_3$, OH, $OCH_3$, and $OCH_2CH_3$;

heteroatoms in the heteroaryl and heterocyclyl represent any heteroatom independently selected from O, N, S, and P, and isotopes thereof;

the halogen is arbitrarily independently selected from F, Cl, Br, and I, and isotopes thereof;

m is an integer arbitrarily selected from 0, 1, 2, 3 and 4;

n is an integer arbitrarily selected from 0, 1, 2, 3 and 4;
P is an integer arbitrarily selected from 0, 1, 2, 3, 4 and 5; and
t is an integer arbitrarily selected from 0, 1, 2, 3, 4 and 5.

2. The quaternary ammonium salt conjugated compound or the pharmaceutically acceptable salt, the solvate, the composition, the enantiomer and the isotope substitution or the double salt thereof according to claim 1, having a structure as represented by formula (IA), formula (IA)

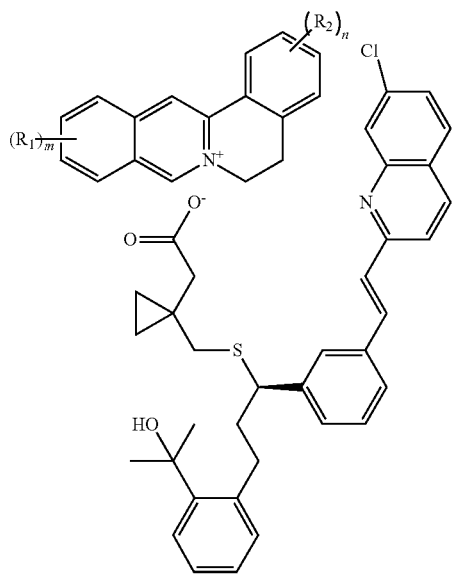

wherein
$R_1$ and $R_2$ are independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally substituted by one to more substituent groups; and the substituent groups are arbitrarily selected from hydrogen, deuterium, halogen, alkyl, haloalkyl, alkoxyl, alkylamino, O═, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent $R_1$ or any two adjacent $R_2$ form 5-6 membered aryl or heteroaryl, 3-8 membered saturated or partially saturated cycloalkyl, and 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, $CF_3$, OH, $OCH_3$, and $OCH_2CH_3$;

heteroatoms in the heteroaryl and heterocyclyl represent any heteroatom independently selected from O, N, S, and P, and isotopes thereof;

the halogen is arbitrarily independently selected from F, Cl, Br, and I, and isotopes thereof;

m is an integer arbitrarily selected from 0, 1, 2, 3 and 4; and n is an integer arbitrarily selected from 0, 1, 2, 3 and 4.

3. The quaternary ammonium salt conjugated compound or the pharmaceutically acceptable salt, the solvate, the composition, the enantiomer and the isotope substitution or the double salt thereof according to claim 1, having a structure as represented by formula (IB), formula (IB)

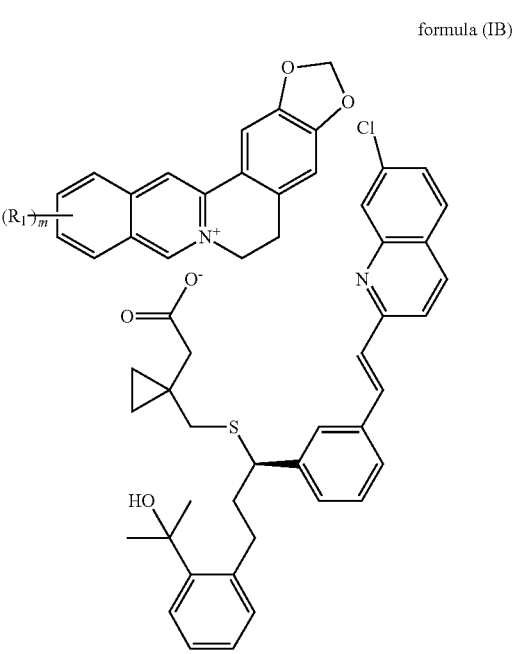

wherein
$R_1$ is independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally substituted by one to more substituent groups; and the substituent groups are arbitrarily selected from hydrogen, deuterium, halogen, alkyl, haloalkyl, alkoxyl, alkylamino, O═, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent $R_1$ form 5-6 membered aryl or heteroaryl, 3-8 membered saturated or partially saturated cycloalkyl, and 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, $CF_3$, OH, $OCH_3$, and $OCH_2CH_3$;

heteroatoms in the heteroaryl and heterocyclyl represent any heteroatom independently selected from O, N, S, and P, and isotopes thereof;

the halogen is arbitrarily independently selected from F, Cl, Br, and I, and isotopes thereof; and m is an integer arbitrarily selected from 0, 1, 2, 3 and 4.

4. The quaternary ammonium salt conjugated compound or the pharmaceutically acceptable salt, the solvate, the composition, the enantiomer and the isotope substitution or the double salt thereof according to claim 2, having a structure as represented by formula (IB),

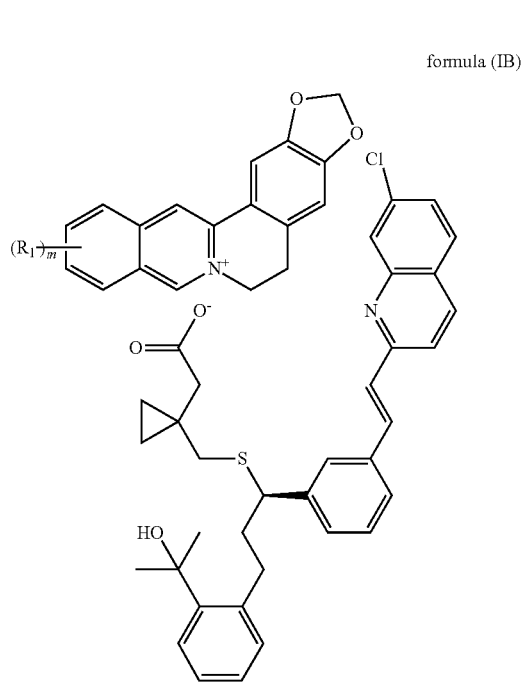

formula (IB)

wherein
R₁ is independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally substituted by one to more substituent groups; and the substituent groups are arbitrarily selected from hydrogen, deuterium, halogen, alkyl, haloalkyl, alkoxyl, alkylamino, O═, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent R₁ form 5-6 membered aryl or heteroaryl, 3-8 membered saturated or partially saturated cycloalkyl, and 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, CF₃, OH, OCH₃, and OCH₂CH₃;

heteroatoms in the heteroaryl and heterocyclyl represent any heteroatom independently selected from O, N, S, and P, and isotopes thereof;

the halogen is arbitrarily independently selected from F, Cl, Br, and I, and isotopes thereof; and m is an integer arbitrarily selected from 0, 1, 2, 3 and 4.

5. The quaternary ammonium salt conjugated compound or the pharmaceutically acceptable salt, the solvate, the composition, the enantiomer and the isotope substitution or the double salt thereof according to claim 1, having a structure as represented by formula (IC),

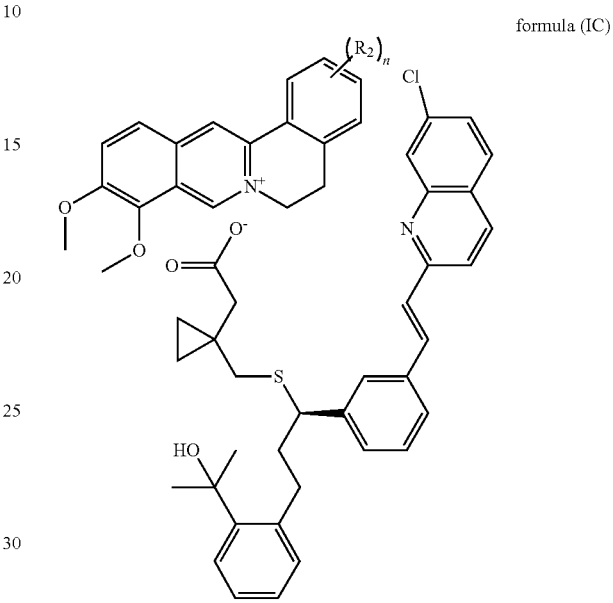

formula (IC)

wherein
R₂ is independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally optimally substituted by one to more substituent groups; and the substituent groups are arbitrarily selected from hydrogen, deuterium, halogen, alkyl, haloalkyl, alkoxyl, alkylamino, O═, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent R₂ form 5-6 membered aryl or heteroaryl, 3-8 membered saturated or partially saturated cycloalkyl, and 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, CF₃, OH, OCH₃, and OCH₂CH₃;

heteroatoms in the heteroaryl and heterocyclyl represent any heteroatom independently selected from O, N, S, and P, and isotopes thereof;

the halogen is arbitrarily independently selected from F, Cl, Br, and I, and isotopes thereof; and n is an integer arbitrarily selected from 0, 1, 2, 3 and 4;

preferably, the quaternary ammonium salt conjugated compound or the pharmaceutically acceptable salt, the solvate, the composition, the enantiomer and the isotope substitution or the double salt thereof, having a structure as represented by formula (ID),

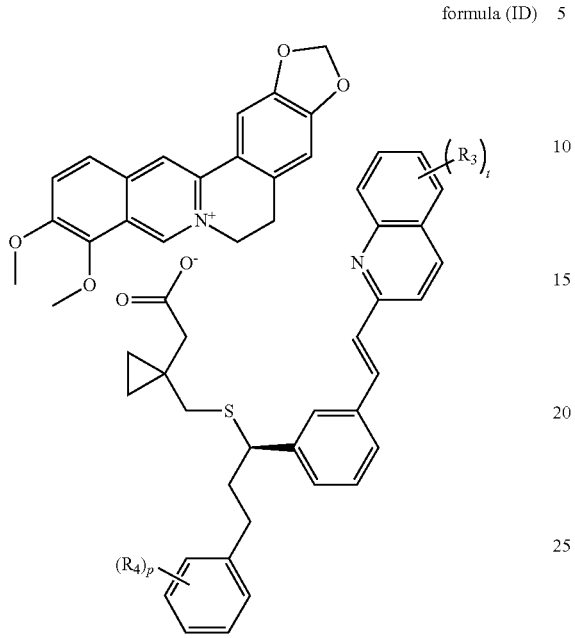

formula (ID)

wherein $R_3$ and $R_4$ are independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally optimally substituted by one to more substituent groups; and the substituent groups are arbitrarily selected from hydrogen, deuterium, halogen, alkyl, haloalkyl, alkoxyl, alkylamino, O=, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent $R_3$ or any two adjacent $R_4$ form 5-6 membered aryl or heteroaryl, 3-8 membered saturated or partially saturated cycloalkyl, 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, $CF_3$, OH, $OCH_3$, and $OCH_2CH_3$;

heteroatoms in the heteroaryl and heterocyclyl represent any heteroatom independently selected from O, N, S, and P, and isotopes thereof;

the halogen is arbitrarily independently selected from F, Cl, Br, and I, and isotopes thereof; and P is an integer arbitrarily selected from 0, 1, 2, 3, 4 and 5; and t is an integer arbitrarily selected from 0, 1, 2, 3, 4 and 5.

6. The quaternary ammonium salt conjugated compound or the pharmaceutically acceptable salt, the solvate, the composition, the enantiomer and the isotope substitution or the double salt thereof according to claim 2, having a structure as represented by formula (IC),

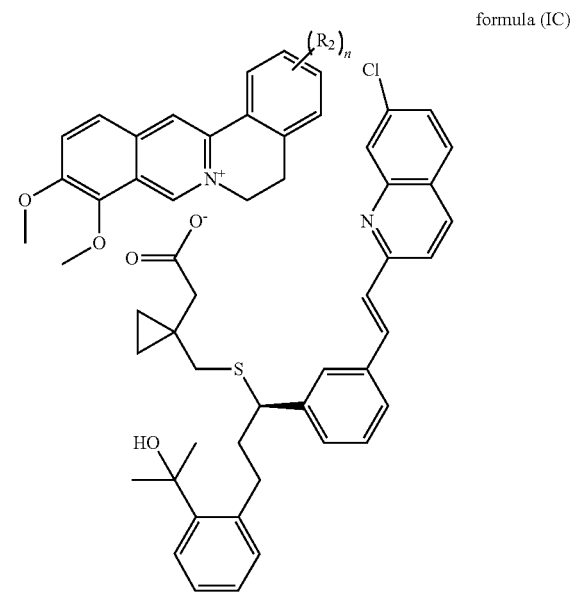

formula (IC)

wherein $R_2$ is independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally optimally substituted by one to more substituent groups; and the substituent groups are arbitrarily selected from hydrogen, deuterium, halogen, alkyl, haloalkyl, alkoxyl, alkylamino, O=, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent $R_2$ form 5-6 membered aryl or heteroaryl, 3-8 membered saturated or partially saturated cycloalkyl, and 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, $CF_3$, OH, $OCH_3$, and $OCH_2CH_3$;

heteroatoms in the heteroaryl and heterocyclyl represent any heteroatom independently selected from O, N, S, and P, and isotopes thereof;

the halogen is arbitrarily independently selected from F, Cl, Br, and I, and isotopes thereof; and n is an integer arbitrarily selected from 0, 1, 2, 3 and 4;

preferably, the quaternary ammonium salt conjugated compound or the pharmaceutically acceptable salt, the solvate, the composition, the enantiomer and the isotope substitution or the double salt thereof, having a structure as represented by formula (ID), formula (ID)

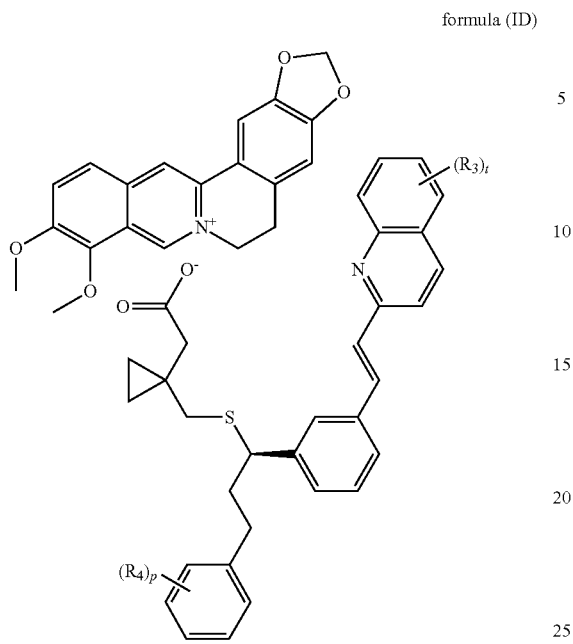

formula (IC)

wherein

R₃ and R₄ are independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally optimally substituted by one to more substituent groups; and the substituent groups are arbitrarily selected from hydrogen, deuterium, halogen, alkyl, haloalkyl, alkoxyl, alkylamino, O=, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent R₃ or any two adjacent R₄ form 5-6 membered aryl or heteroaryl, 3-8 membered saturated or partially saturated cycloalkyl, 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, $CF_3$, OH, $OCH_3$, and $OCH_2CH_3$;

heteroatoms in the heteroaryl and heterocyclyl represent any heteroatom independently selected from O, N, S, and P, and isotopes thereof;

the halogen is arbitrarily independently selected from F, Cl, Br, and I, and isotopes thereof; and P is an integer arbitrarily selected from 0, 1, 2, 3, 4 and 5; and t is an integer arbitrarily selected from 0, 1, 2, 3, 4 and 5.

7. The quaternary ammonium salt conjugated compound or the pharmaceutically acceptable salt, the solvate, the composition, the enantiomer and the isotope substitution or the double salt thereof according to claim 3, having a structure as represented by formula (IC), wherein R₂ is independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally optimally substituted by one to more substituent groups; and the substituent groups are arbitrarily selected from hydrogen, deuterium, halogen, alkyl, haloalkyl, alkoxyl, alkylamino, O=, CN, OH, $C_{3-10}$ saturated or partially saturated cycloalkyl, $C_{3-10}$ saturated or partially saturated heterocyclyl, 6-10 membered aryl and 5-8 membered heteroaryl; or any two adjacent R₂ form 5-6 membered aryl or heteroaryl, 3-8 membered saturated or partially saturated cycloalkyl, and 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, $CF_3$, OH, $OCH_3$, and $OCH_2CH_3$;

heteroatoms in the heteroaryl and heterocyclyl represent any heteroatom independently selected from O, N, S, and P, and isotopes thereof;

the halogen is arbitrarily independently selected from F, Cl, Br, and I, and isotopes thereof; and n is an integer arbitrarily selected from 0, 1, 2, 3 and 4;

preferably, the quaternary ammonium salt conjugated compound or the pharmaceutically acceptable salt, the solvate, the composition, the enantiomer and the isotope substitution or the double salt thereof, having a structure as represented by formula (ID), formula (ID)

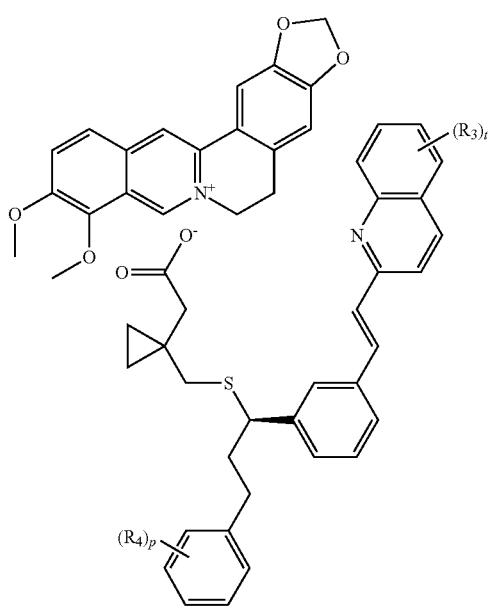

wherein
R₃ and R₄ are independently selected from hydrogen, deuterium, halogen, —CN, $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl, wherein the $C_{1-10}$ alkyl, $C_{2-10}$ alkenyl, $C_{2-10}$ alkynyl, $C_{1-10}$ alkoxyl, 6-10 membered aryl, 5-8 membered heteroaryl, 3-8 membered saturated or partially saturated cycloalkyl and 3-8 membered saturated or partially saturated heterocyclyl are optionally optimally substituted by one to more substituent groups; and the substituent groups are arbitrarily selected from hydrogen, deuterium, halogen, alkyl, haloalkyl, alkoxyl, alkylamino, O=, CN, OH, $C_{3-10}$ saturated or partially saturated cycloalkyl, $C_{3-10}$ saturated or partially saturated heterocyclyl, 6-10 membered aryl and 5-8 membered heteroaryl; or
any two adjacent R₃ or any two adjacent R₄ form 5-6 membered aryl or heteroaryl, 3-8 membered saturated or partially saturated cycloalkyl, 3-8 membered saturated or partially saturated heterocyclyl together with carbon attached thereto, wherein the cycloalkyl and the heterocyclyl are optionally substituted by one to more groups selected from hydrogen, deuterium, halogen, oxo, CN, CF₃, OH, OCH₃, and OCH₂CH₃;
heteroatoms in the heteroaryl and heterocyclyl represent any heteroatom independently selected from O, N, S, and P, and isotopes thereof;
the halogen is arbitrarily independently selected from F, Cl, Br, and I, and isotopes thereof; and
P is an integer arbitrarily selected from 0, 1, 2, 3, 4 and 5; and
t is an integer arbitrarily selected from 0, 1, 2, 3, 4 and 5.

8. The quaternary ammonium salt conjugated compound or the pharmaceutically acceptable salt, the solvate, the composition, the enantiomer and the isotope substitution or the double salt thereof according to claim 1, wherein each R₁ is the same or different, and is each independently selected from hydrogen, $C_{1-6}$ alkyl, and $C_{1-6}$ alkoxyl; or two R₁ form a 3-8 membered heterocyclic ring together with carbons respectively connected thereto;
each R₁ is the same or different, and is each independently selected from hydrogen, methyl or methoxyl; or two R₁ form

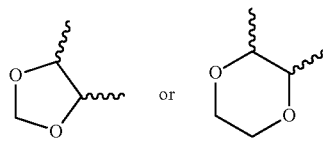

together with carbons respectively connected thereto;
each R₂ is the same or different, and is each independently selected from hydrogen, $C_{1-6}$ alkyl, and $C_{1-6}$ alkoxyl; or two R₂ form a 3-8 membered heterocyclic ring together with carbons respectively connected thereto;
each R₂ is the same or different, and is each independently selected from hydrogen, methyl or methoxyl; or two R₂ form

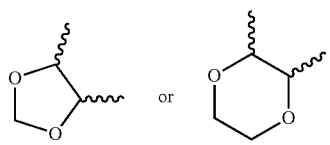

together with carbons respectively connected thereto;
each R₃ is the same or different, and is each independently selected from hydrogen, hydrogen, $C_{1-6}$ alkyl, and $C_{1-6}$ alkoxyl;
each R₃ is the same or different, and is each independently selected from fluorine, chlorine, bromine or iodine, preferably chlorine;
each R₄ is the same or different, and is each independently selected from hydrogen or hydroxy $C_{1-6}$ alkyl;
R₄ is selected from hydrogen or

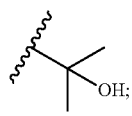 [SMILES: *C(C)(C)O]

m is selected from 0, 1, 2 or 3;
n is selected from 0, 1, 2, or 3;
t is selected from 0 or 1; and
p is selected from 0 or 1.

9. The quaternary ammonium salt conjugated compound or the pharmaceutically acceptable salt, the solvate, the composition, the enantiomer and the isotope substitution or the double salt thereof according to claim 2, wherein each R₁ is the same or different, and is each independently selected from hydrogen, $C_{1-6}$ alkyl, and $C_{1-6}$ alkoxyl; or two R₁ form a 3-8 membered heterocyclic ring together with carbons respectively connected thereto;
each R₁ is the same or different, and is each independently selected from hydrogen, methyl or methoxyl; or two R₁ form

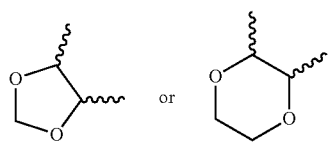

together with carbons respectively connected thereto;
each $R_2$ is the same or different, and is each independently selected from hydrogen, $C_{1-6}$ alkyl, and $C_{1-6}$ alkoxyl; or two $R_2$ form a 3-8 membered heterocyclic ring together with carbons respectively connected thereto;
each $R_2$ is the same or different, and is each independently selected from hydrogen, methyl or methoxyl; or two $R_2$ form

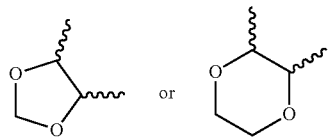

together with carbons respectively connected thereto;
each $R_3$ is the same or different, and is each independently selected from hydrogen, hydrogen, $C_{1-6}$ alkyl, and $C_{1-6}$ alkoxyl;
each $R_3$ is the same or different, and is each independently selected from fluorine, chlorine, bromine or iodine, preferably chlorine;
each $R_4$ is the same or different, and is each independently selected from hydrogen or hydroxy $C_{1-6}$ alkyl;
$R_4$ is selected from hydrogen or

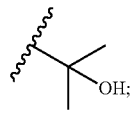

m is selected from 0, 1, 2 or 3;
n is selected from 0, 1, 2, or 3;
t is selected from 0 or 1; and
p is selected from 0 or 1.

10. The quaternary ammonium salt conjugated compound or the pharmaceutically acceptable salt, the solvate, the composition, the enantiomer and the isotope substitution or the double salt thereof according to claim 3, wherein each $R_1$ is the same or different, and is each independently selected from hydrogen, $C_{1-6}$ alkyl, and $C_{1-6}$ alkoxyl; or two $R_1$ form a 3-8 membered heterocyclic ring together with carbons respectively connected thereto;
each $R_1$ is the same or different, and is each independently selected from hydrogen, methyl or methoxyl; or two $R_1$ form

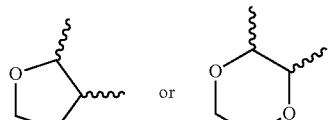

together with carbons respectively connected thereto;
each $R_2$ is the same or different, and is each independently selected from hydrogen, $C_{1-6}$ alkyl, and $C_{1-6}$ alkoxyl; or two $R_2$ form a 3-8 membered heterocyclic ring together with carbons respectively connected thereto;
each $R_2$ is the same or different, and is each independently selected from hydrogen, methyl or methoxyl; or two $R_2$ form

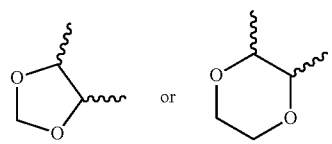

together with carbons respectively connected thereto;
each $R_3$ is the same or different, and is each independently selected from hydrogen, hydrogen, $C_{1-6}$ alkyl, and $C_{1-6}$ alkoxyl;
each $R_3$ is the same or different, and is each independently selected from fluorine, chlorine, bromine or iodine, preferably chlorine;
each $R_4$ is the same or different, and is each independently selected from hydrogen or hydroxy $C_{1-6}$ alkyl;
$R_4$ is selected from hydrogen or

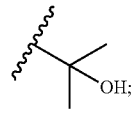 [SMILES: *C(C)(C)O]

m is selected from 0, 1, 2 or 3;
n is selected from 0, 1, 2, or 3;
t is selected from 0 or 1; and
p is selected from 0 or 1.

11. The quaternary ammonium salt conjugated compound or the pharmaceutically acceptable salt, the solvate, the composition, the enantiomer and the isotope substitution or the double salt thereof according to claim 4, wherein each $R_1$ is the same or different, and is each independently selected from hydrogen, $C_{1-6}$ alkyl, and $C_{1-6}$ alkoxyl; or two $R_1$ form a 3-8 membered heterocyclic ring together with carbons respectively connected thereto;
each $R_1$ is the same or different, and is each independently selected from hydrogen, methyl or methoxyl; or two $R_1$ form

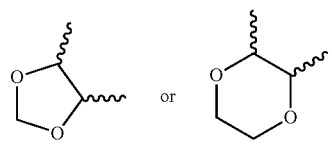

together with carbons respectively connected thereto;
each $R_2$ is the same or different, and is each independently selected from hydrogen, $C_{1-6}$ alkyl, and $C_{1-6}$ alkoxyl; or two $R_2$ form a 3-8 membered heterocyclic ring together with carbons respectively connected thereto;
each $R_2$ is the same or different, and is each independently selected from hydrogen, methyl or methoxyl; or two $R_2$ form

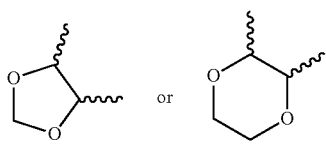
or together with carbons respectively connected thereto;
 each $R_3$ is the same or different, and is each independently selected from hydrogen, hydrogen, $C_{1-6}$ alkyl, and $C_{1-6}$ alkoxyl;
 each $R_3$ is the same or different, and is each independently selected from fluorine, chlorine, bromine or iodine, preferably chlorine;
 each $R_4$ is the same or different, and is each independently selected from hydrogen or hydroxy $C_{1-6}$ alkyl;
 $R_4$ is selected from hydrogen or

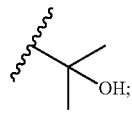

m is selected from 0, 1, 2 or 3;
 n is selected from 0, 1, 2, or 3;
 t is selected from 0 or 1; and
 p is selected from 0 or 1.

12. The quaternary ammonium salt conjugated compound or the pharmaceutically acceptable salt, the solvate, the composition, the enantiomer and the isotope substitution or the double salt thereof according to any one of claims claim 1, which is selected from the following structural compound or a corresponding enantiomer or composition thereof.

Compound 1

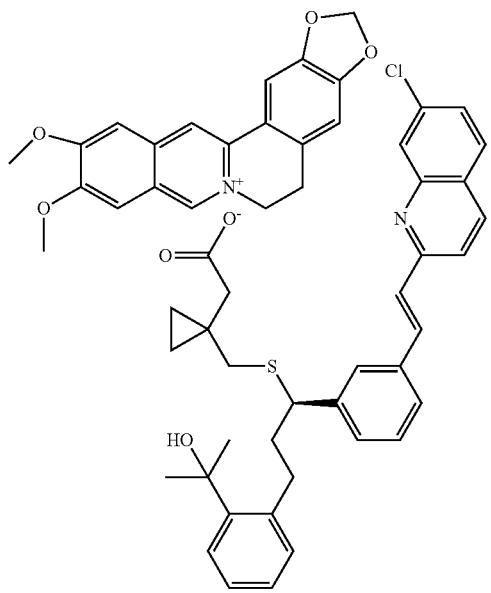

Compound 2

Compound 3

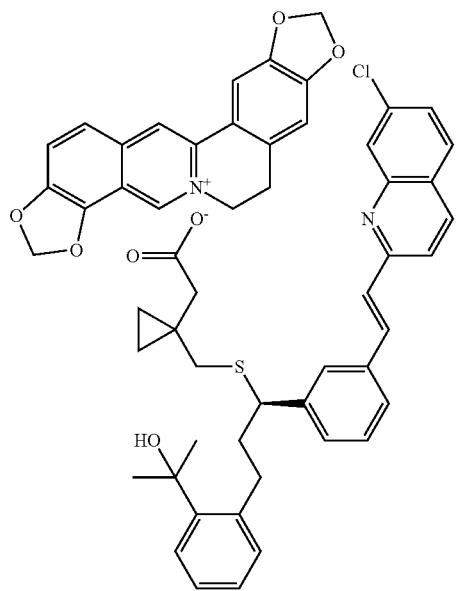

-continued
Compound 4
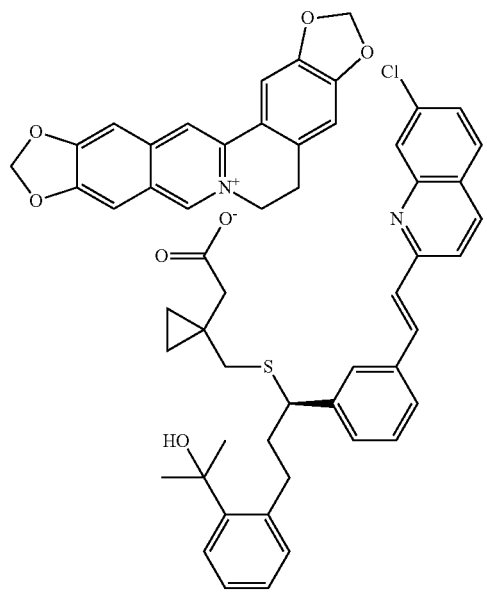
Compound 5
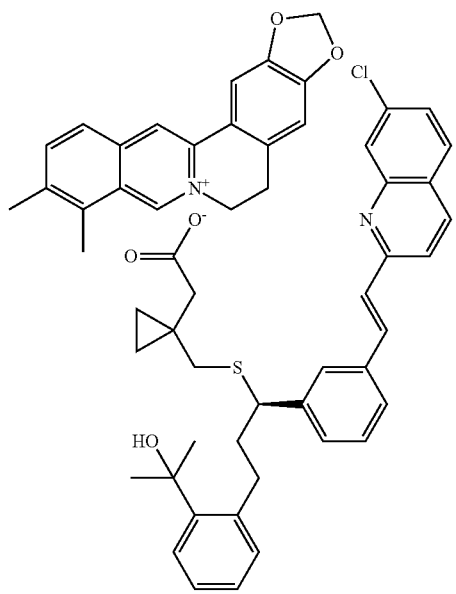
-continued
Compound 6
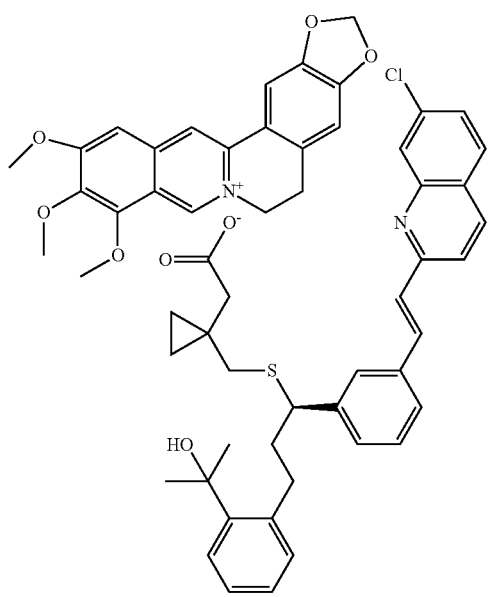
Compound 7
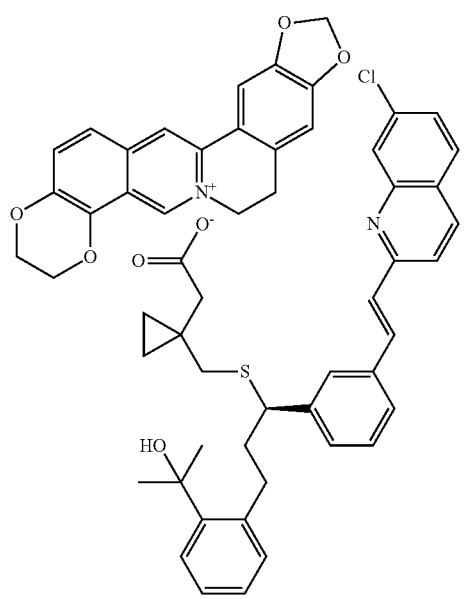

Compound 8
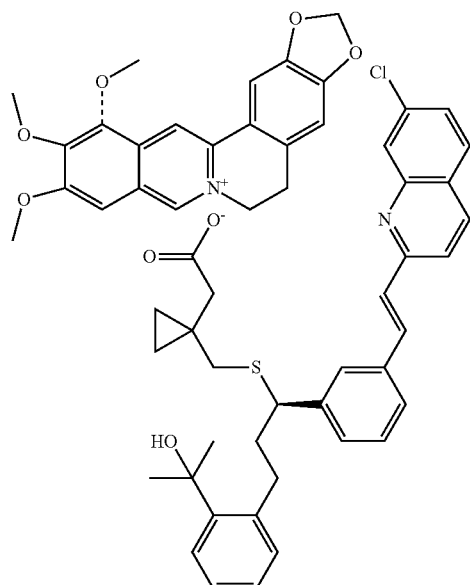
Compound 10
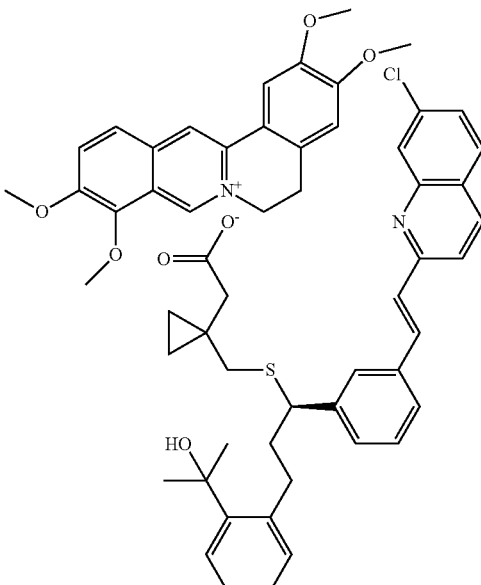
Compound 9
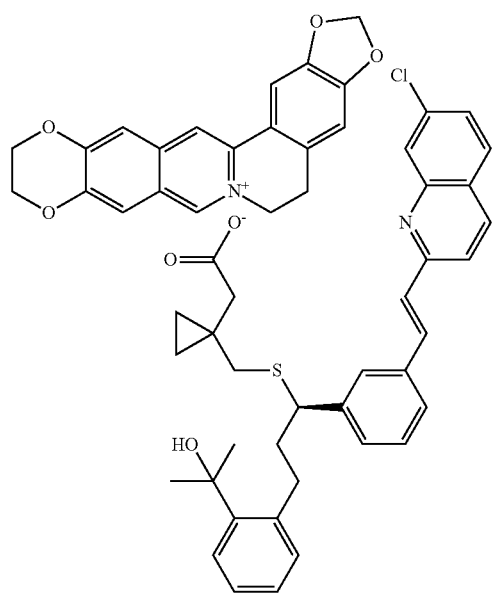
Compound 11
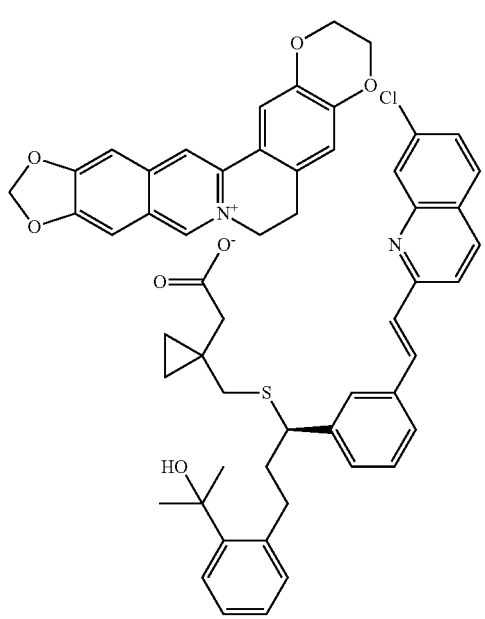

Compound 12

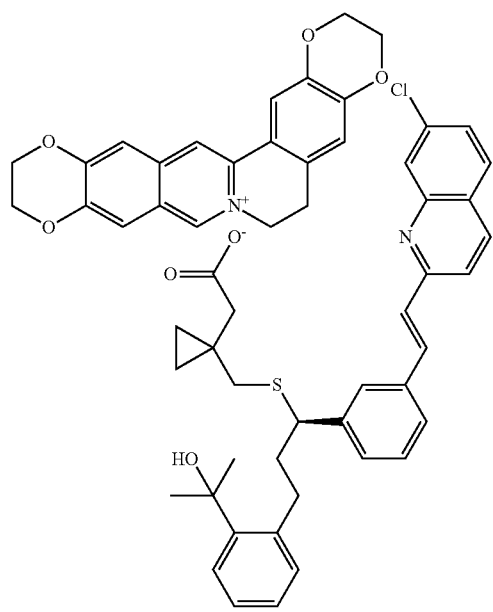

Compound 14

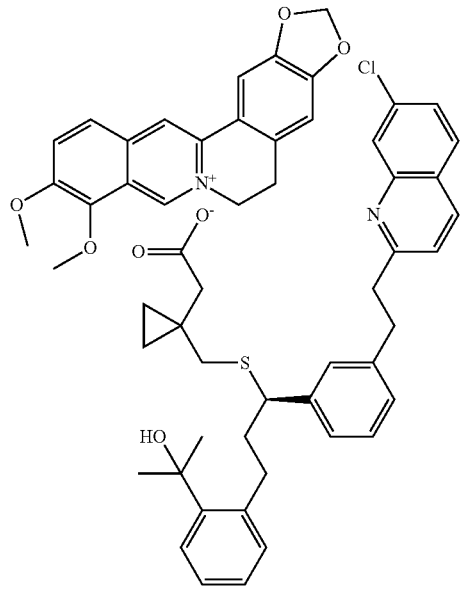

Compound 15

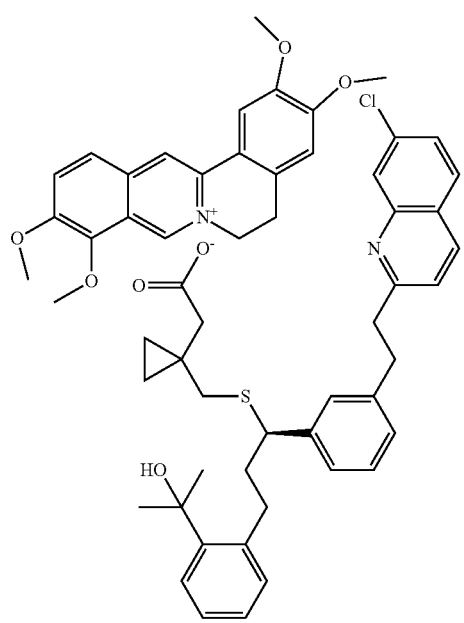

Compound 13

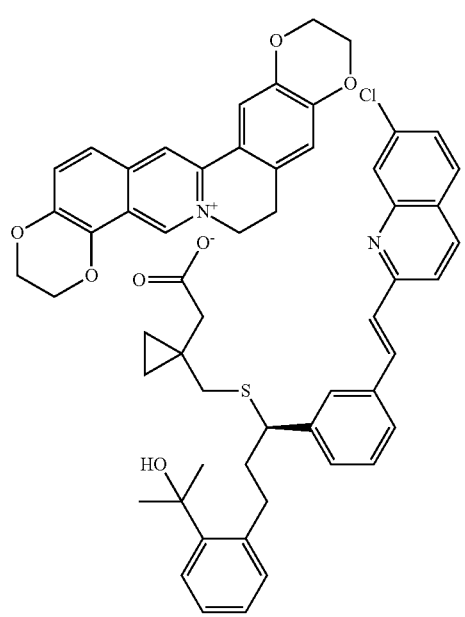

13. The quaternary ammonium salt conjugated compound or the pharmaceutically acceptable salt, the solvate, the composition, the enantiomer and the isotope substitution or the double salt thereof according to any one of claims claim 2, which is selected from the following structural compound or a corresponding enantiomer or composition thereof.

Compound 1
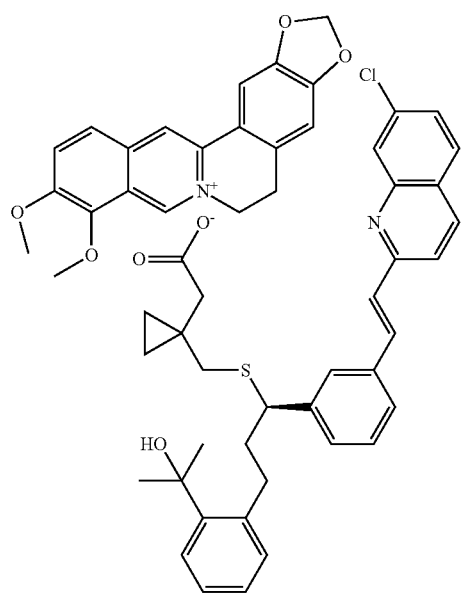
Compound 3
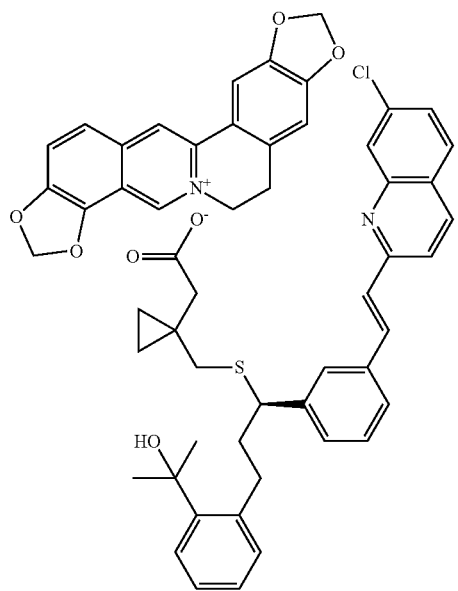
Compound 2
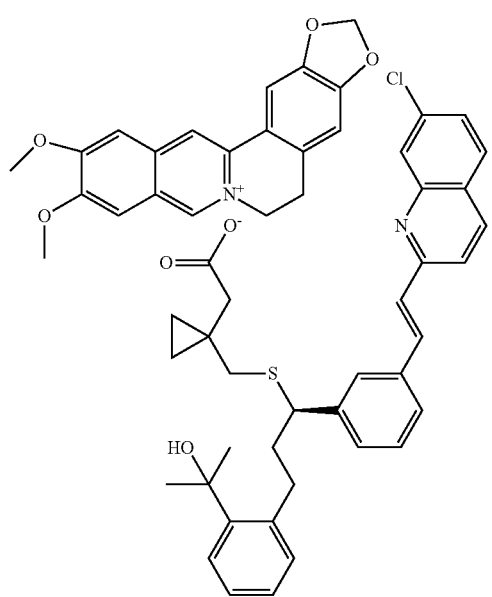
Compound 4
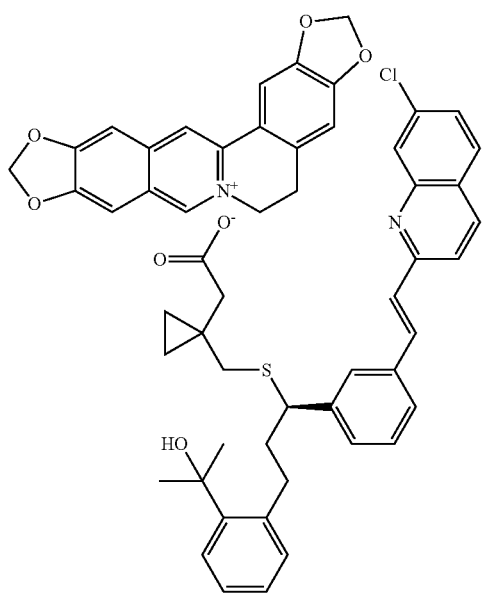

Compound 5
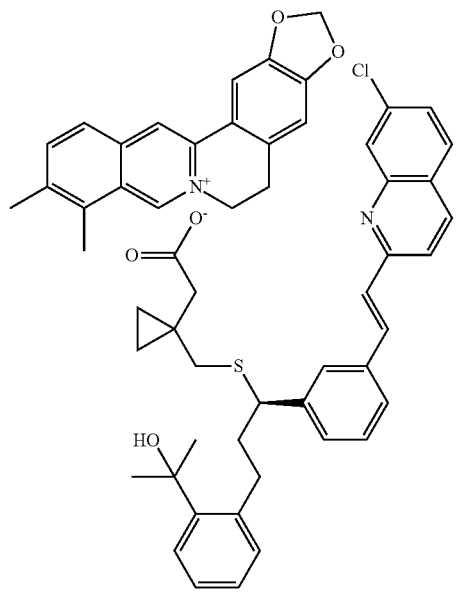
Compound 7
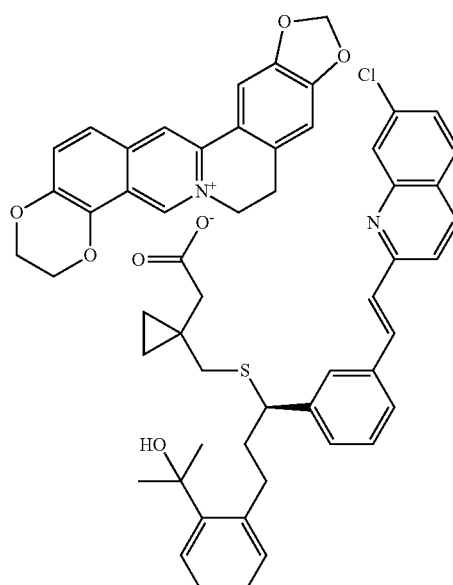
Compound 6
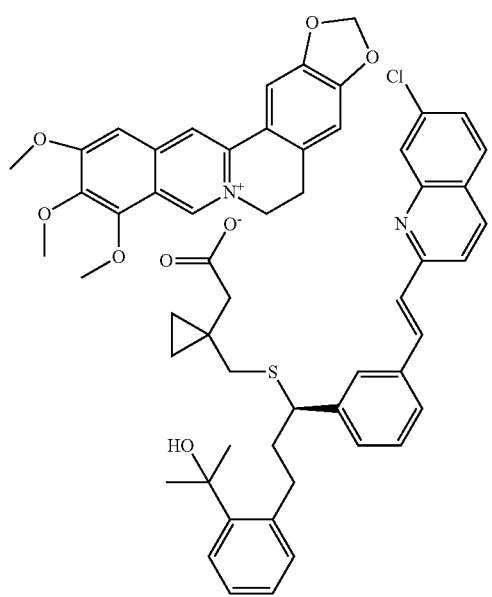
Compound 8
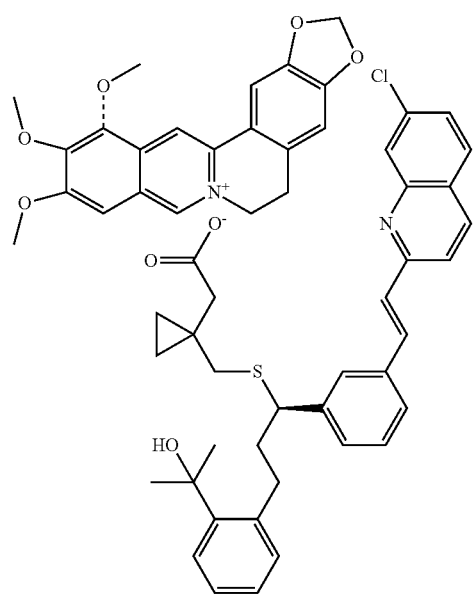

Compound 9
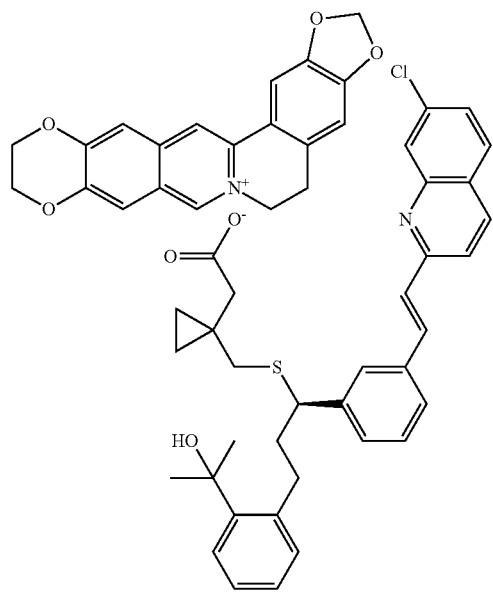
Compound 10
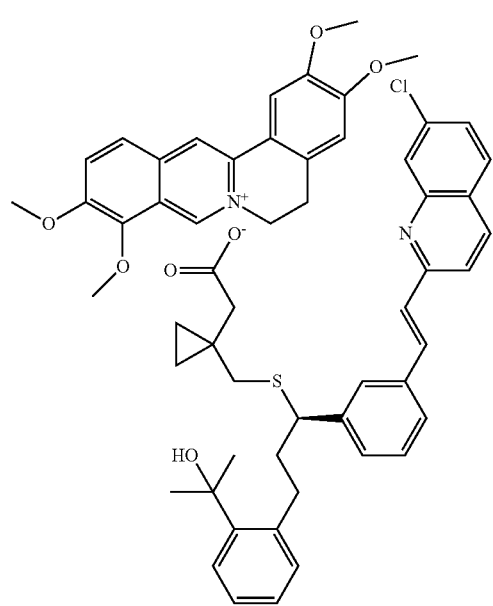
Compound 11
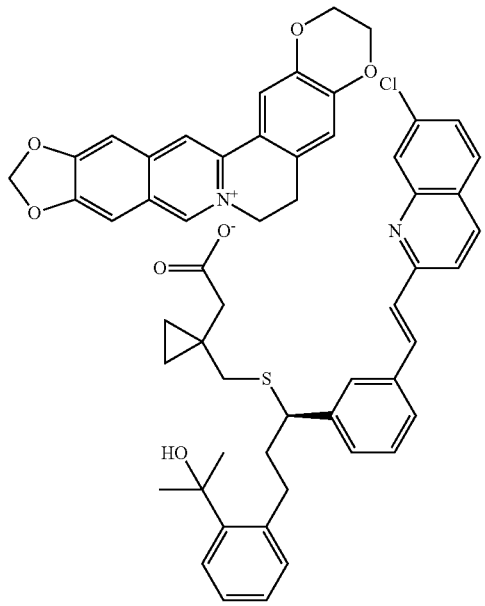
Compound 12
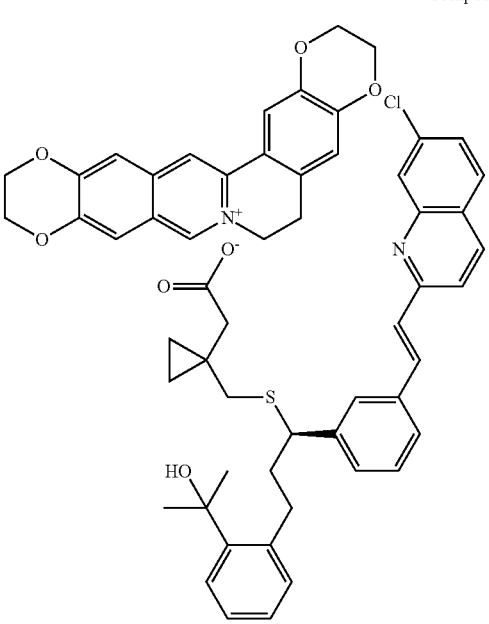

Compound 13

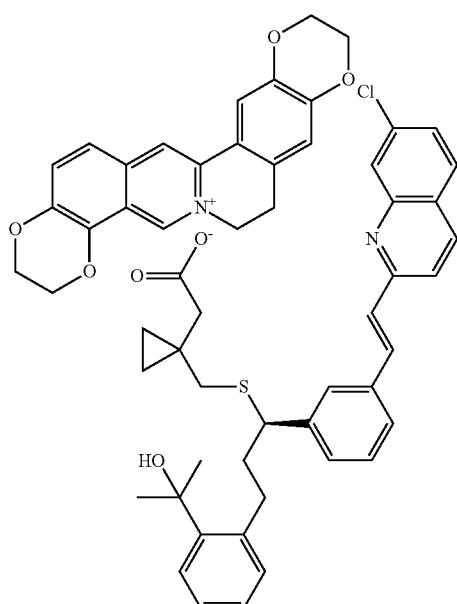

Compound 14

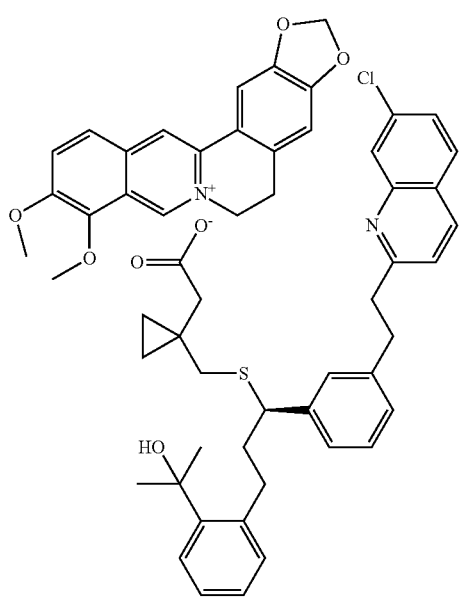

Compound 15

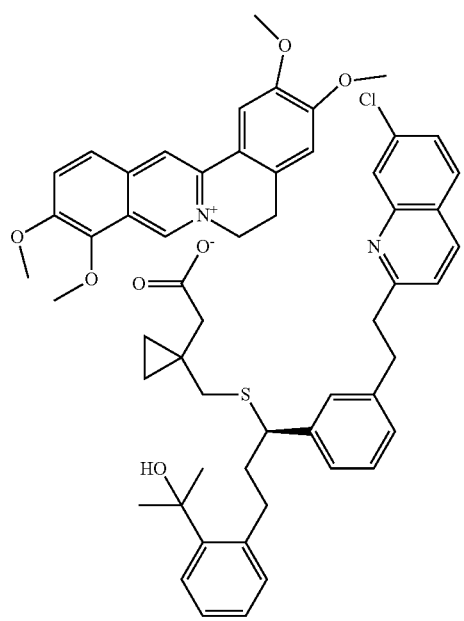

14. The quaternary ammonium salt conjugated compound or the pharmaceutically acceptable salt, the solvate, the composition, the enantiomer and the isotope substitution or the double salt thereof according to any one of claims claim 3, which is selected from the following structural compound or a corresponding enantiomer or composition thereof.

Compound 1

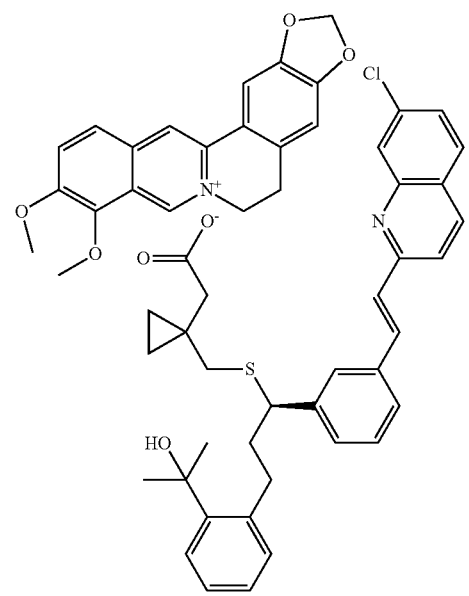

Compound 2
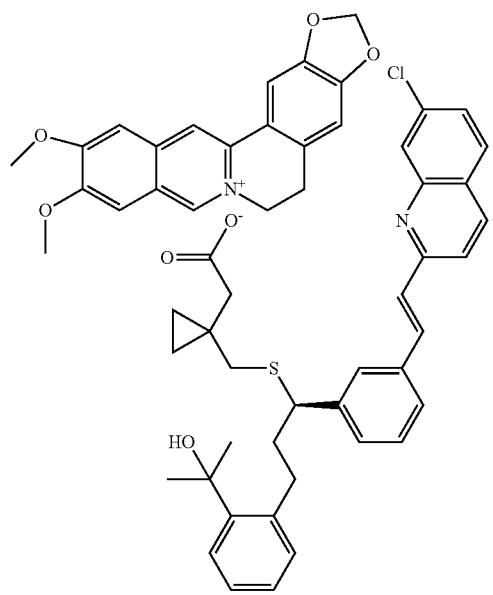
Compound 3
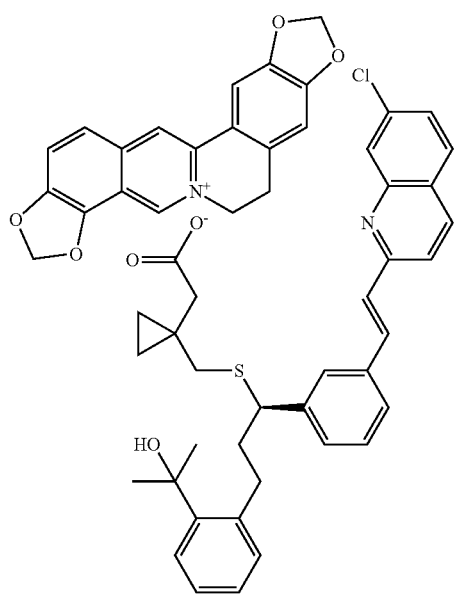
Compound 4
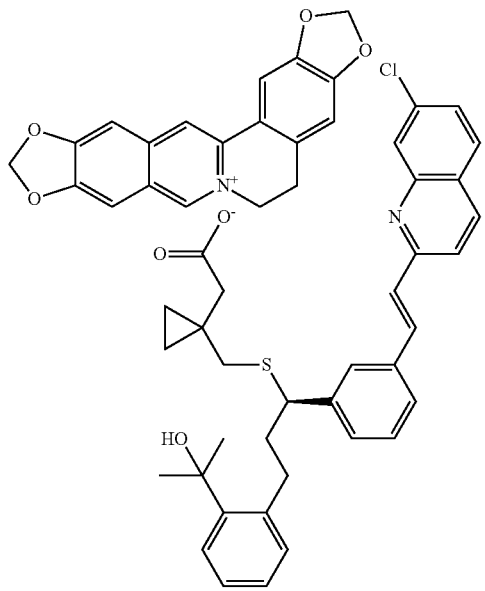
Compound 5
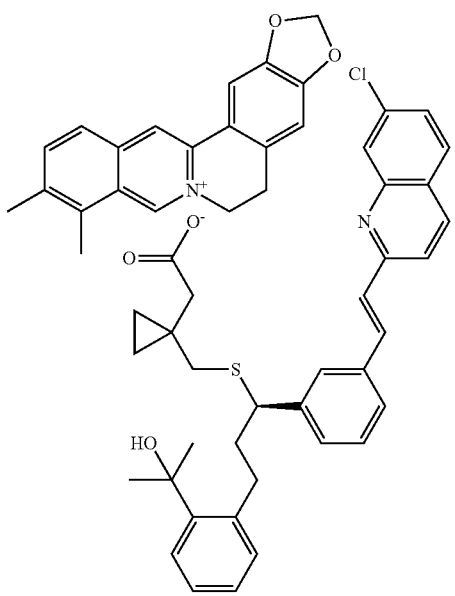

Compound 6
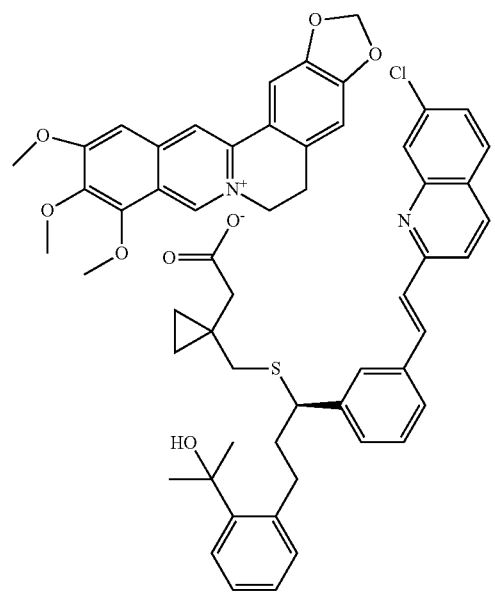
Compound 8
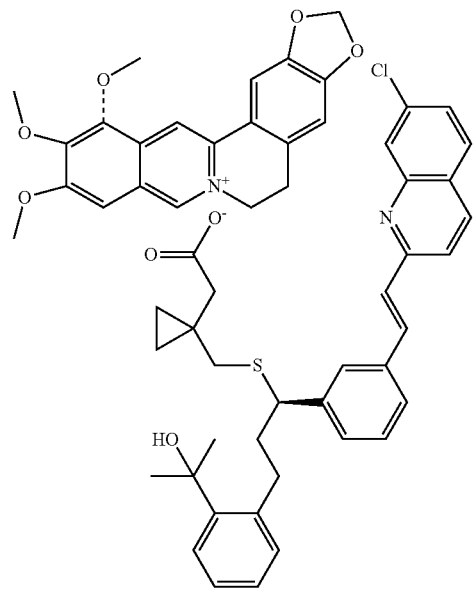
Compound 7
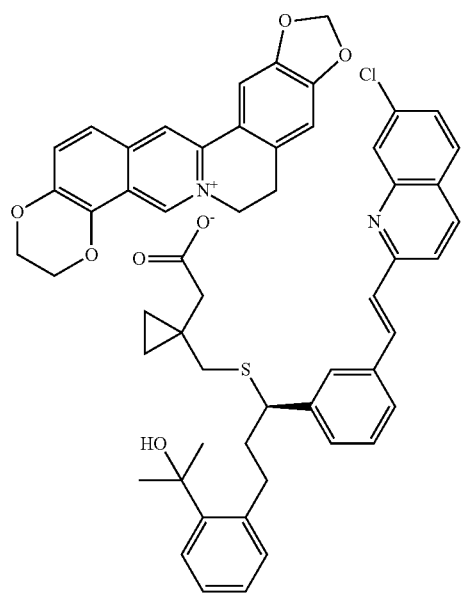
Compound 9
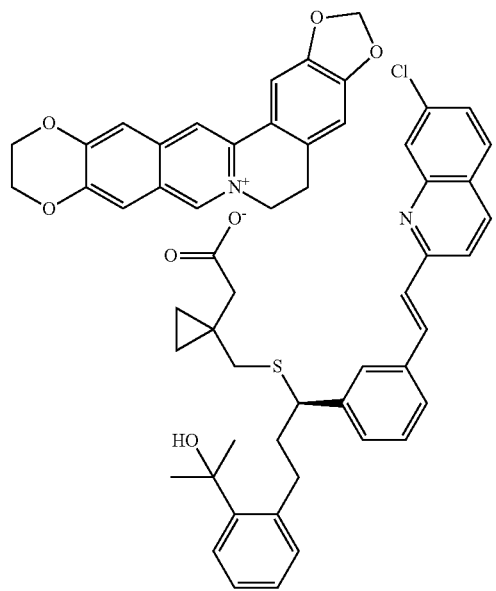

Compound 10
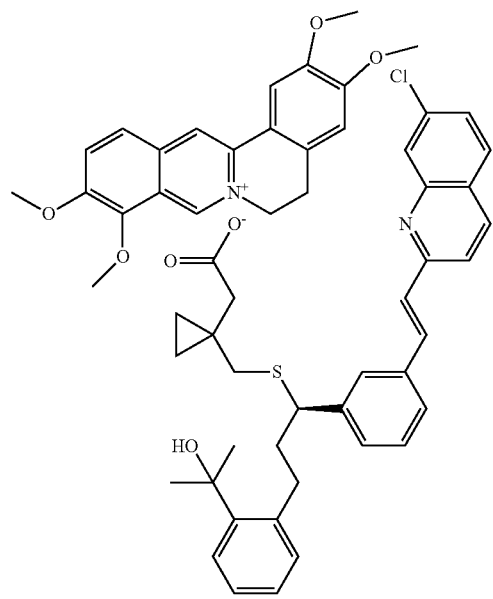
Compound 12
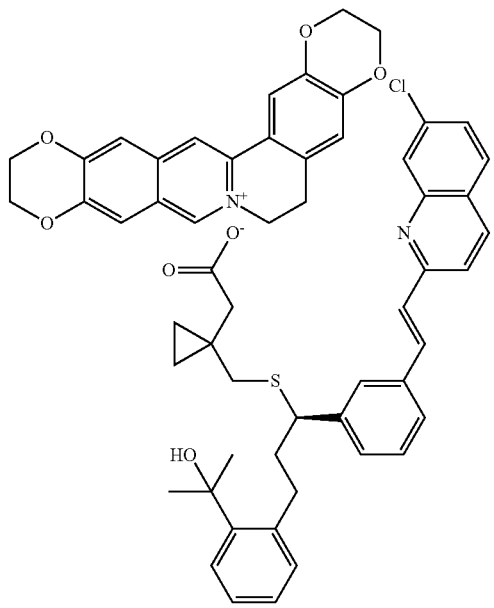
Compound 11
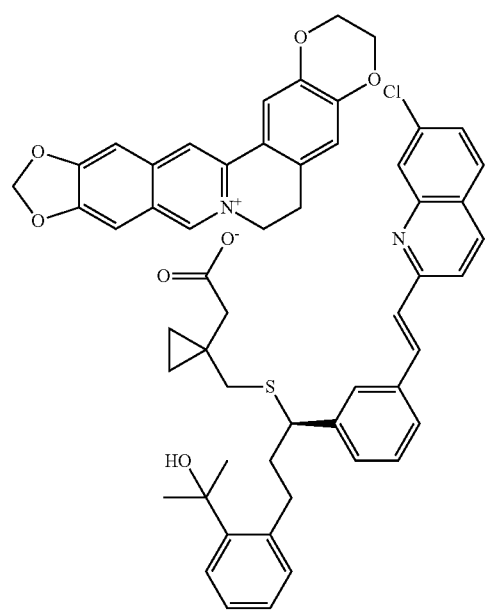
Compound 13
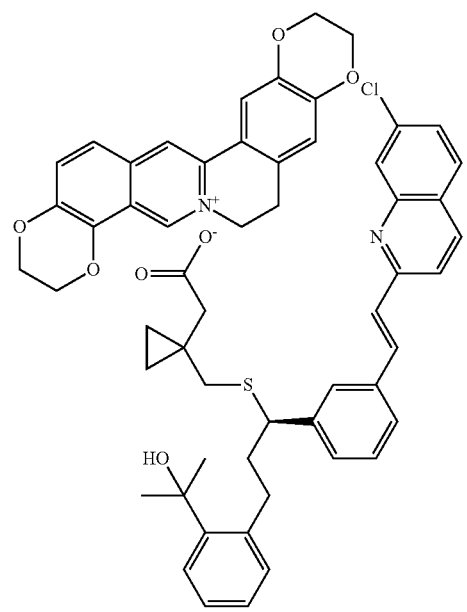

Compound 14

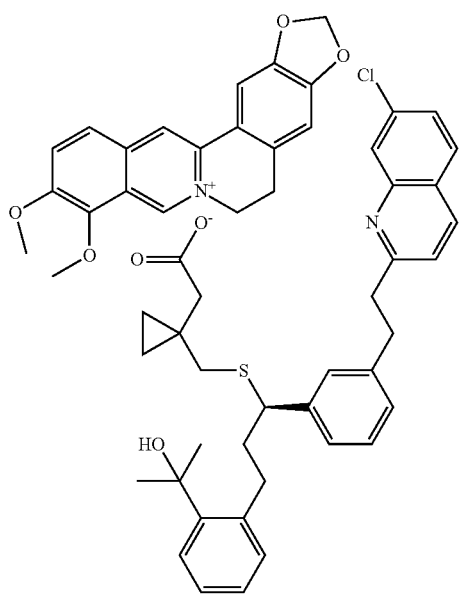

Compound 15

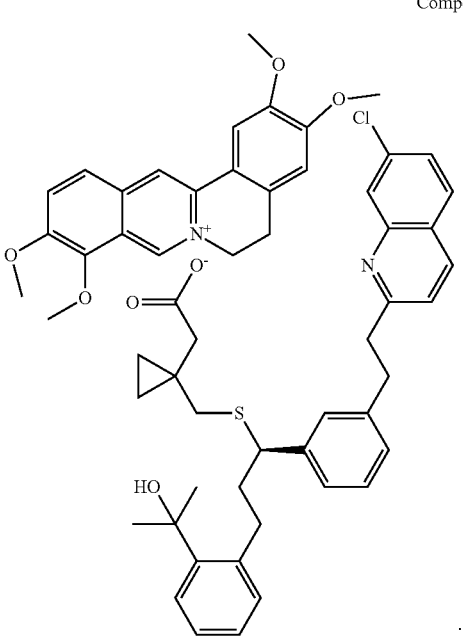

Compound 1

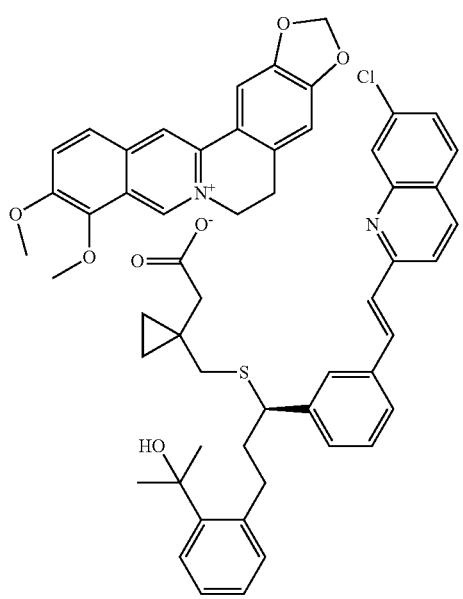

Compound 2

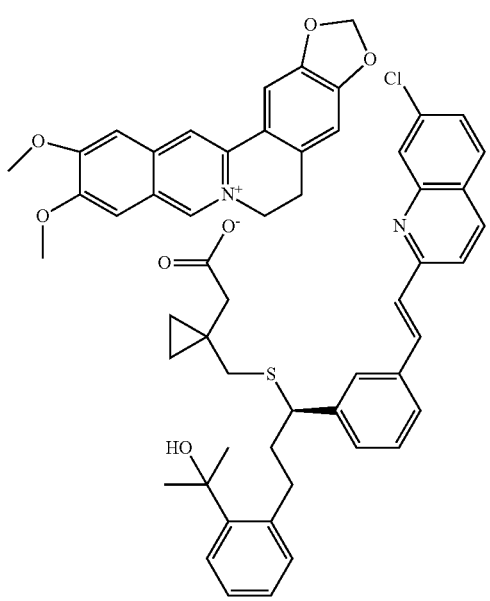

15. The quaternary ammonium salt conjugated compound or the pharmaceutically acceptable salt, the solvate, the composition, the enantiomer and the isotope substitution or the double salt thereof according to any one of claims claim 4, which is selected from the following structural compound or a corresponding enantiomer or composition thereof.

-continued
Compound 3
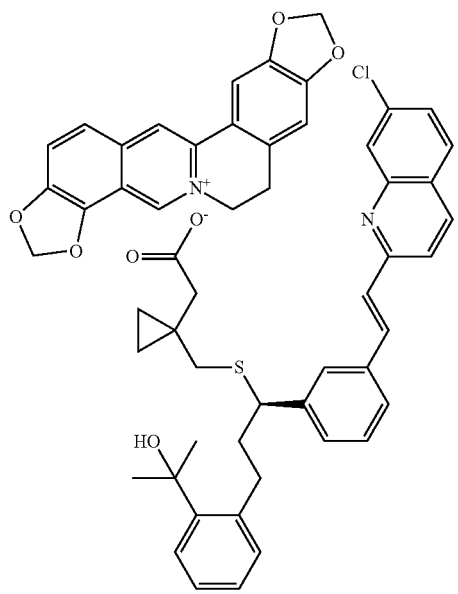
Compound 4
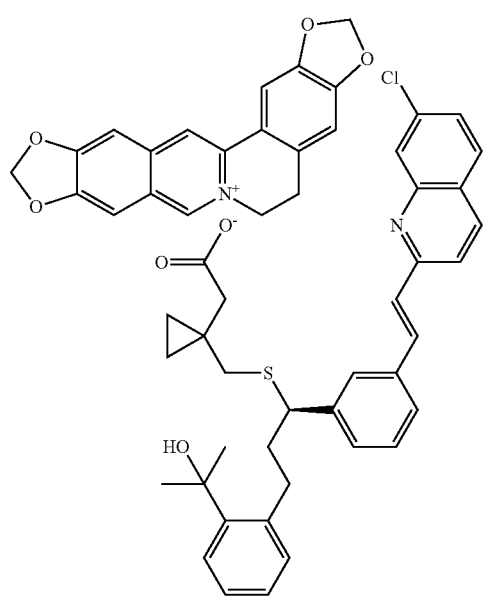
Compound 5
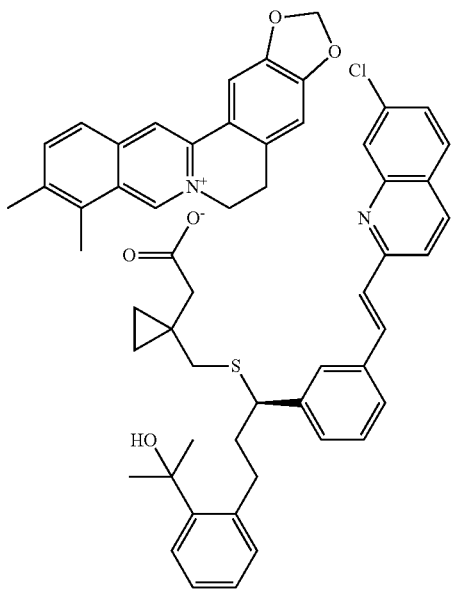
Compound 6
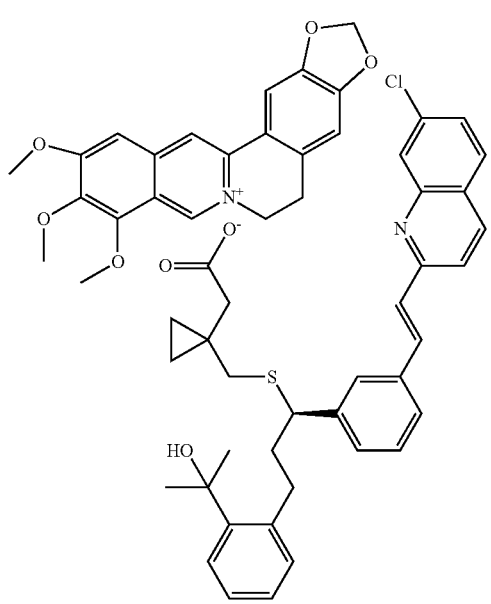

Compound 7
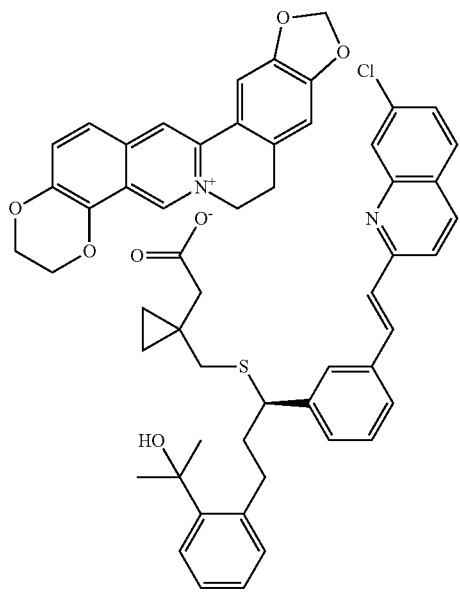
Compound 9
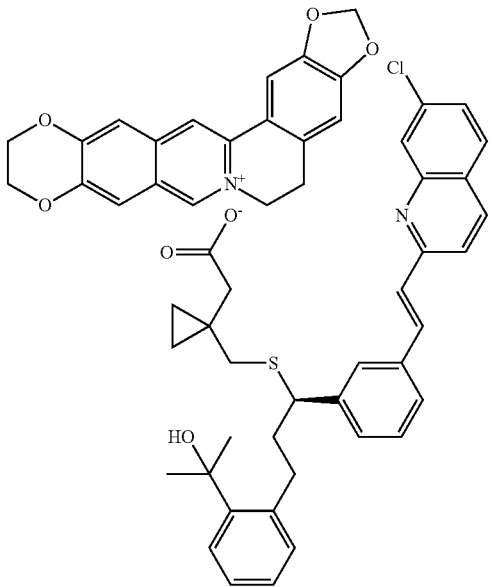
Compound 8
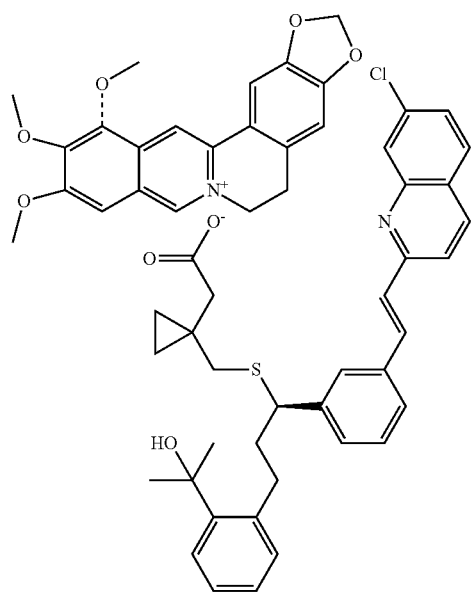
Compound 10
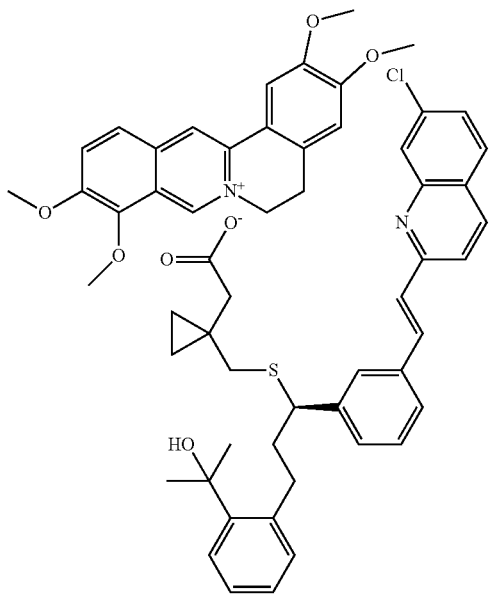

Compound 11
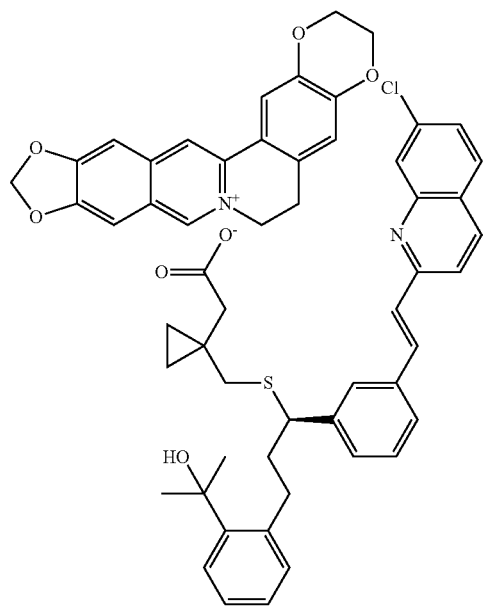
Compound 13
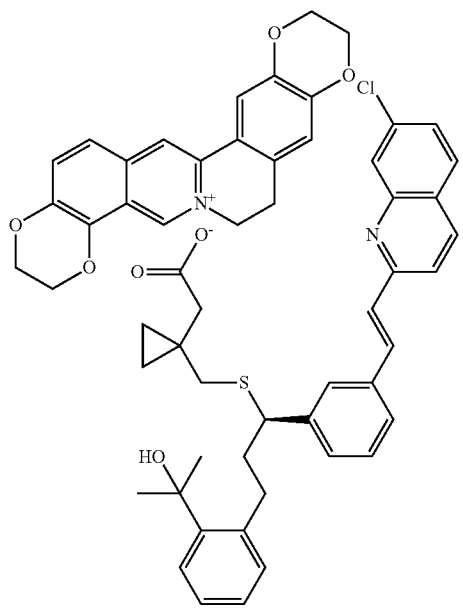
Compound 12
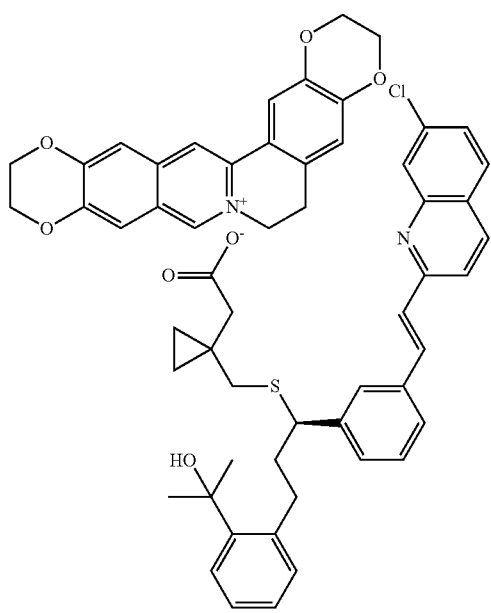
Compound 14
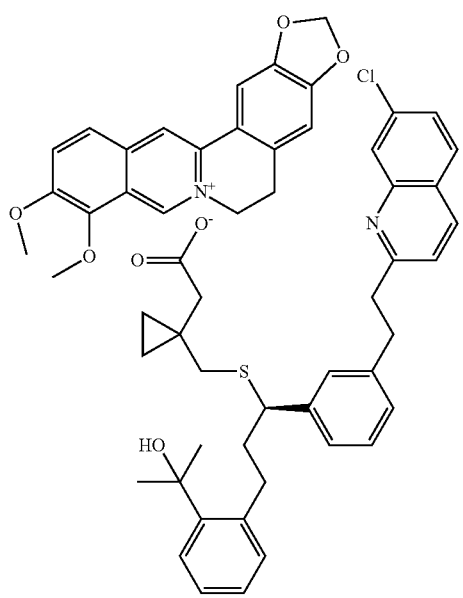

Compound 15

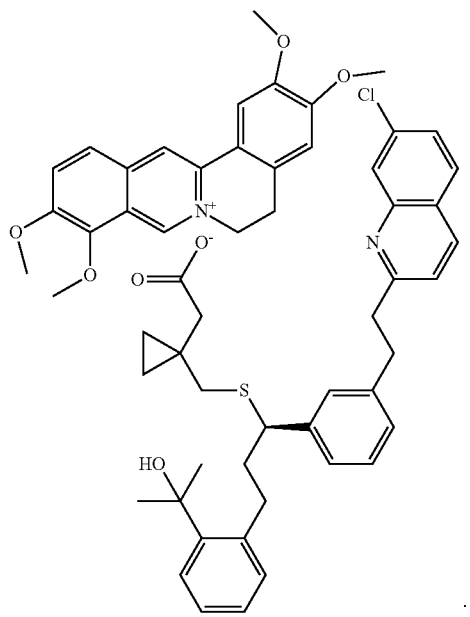

Compound 2

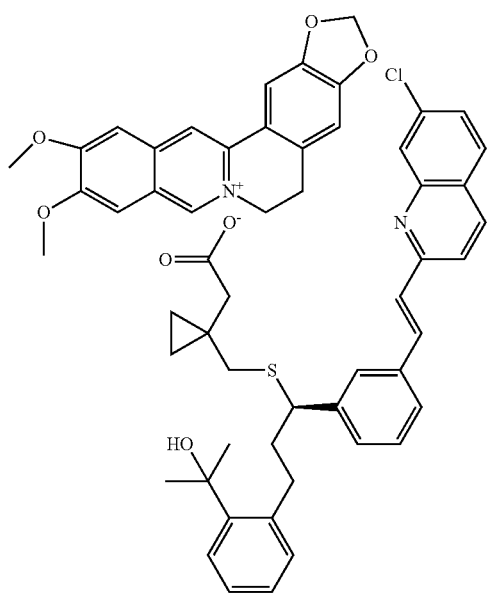

16. The quaternary ammonium salt conjugated compound or the pharmaceutically acceptable salt, the solvate, the composition, the enantiomer and the isotope substitution or the double salt thereof according to any one of claims claim 5, which is selected from the following structural compound or a corresponding enantiomer or composition thereof.

Compound 1

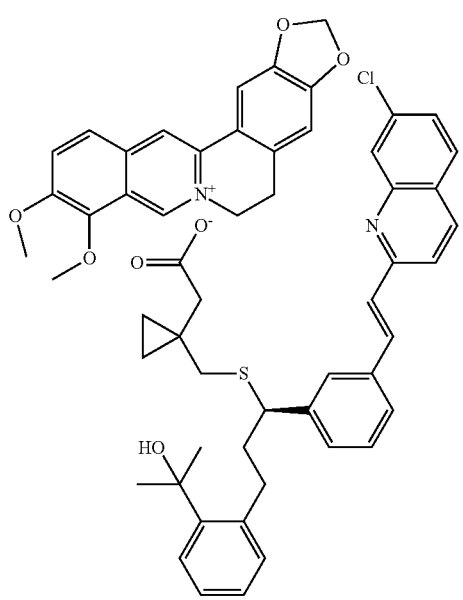

Compound 3

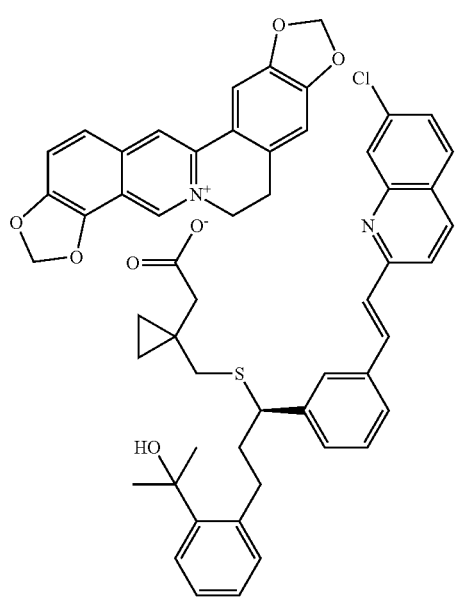

Compound 4
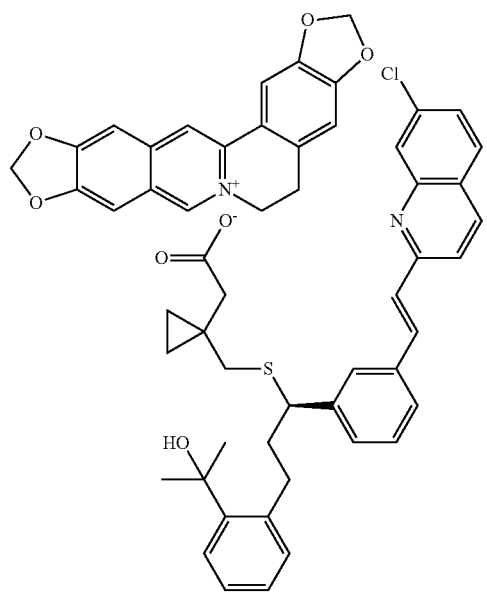
Compound 6
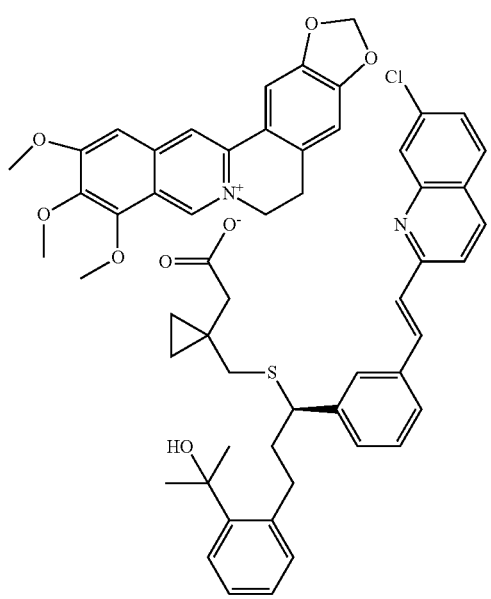
Compound 5
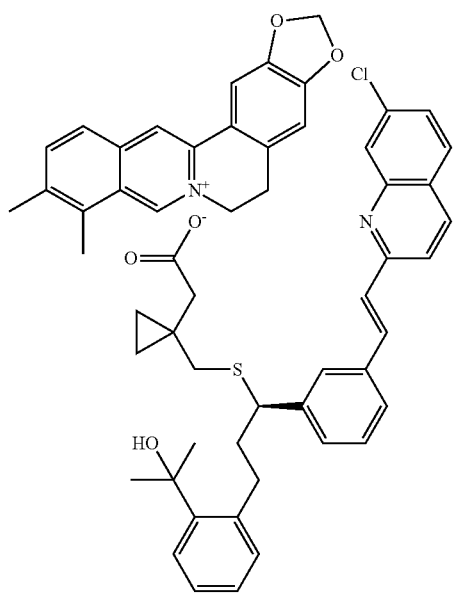
Compound 7
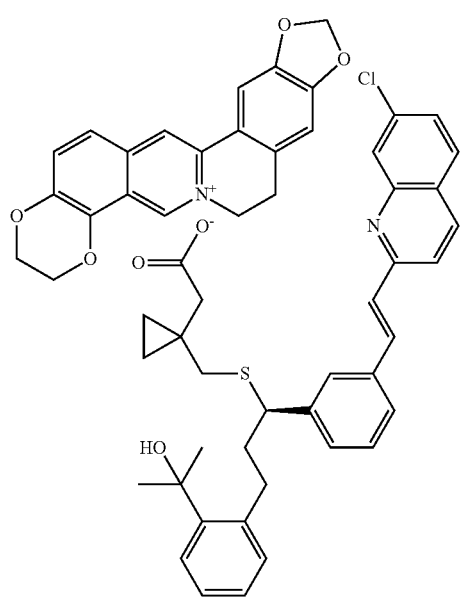

Compound 8
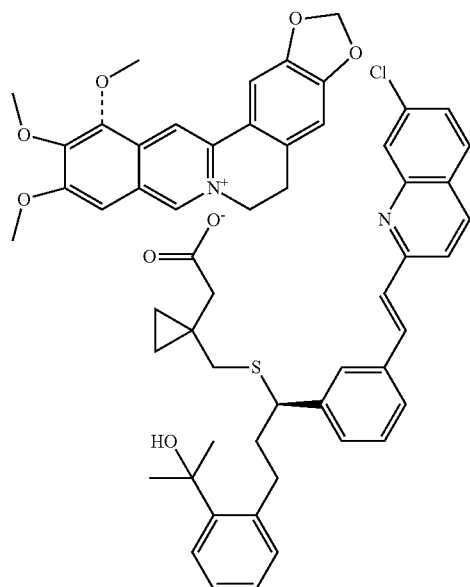
Compound 10
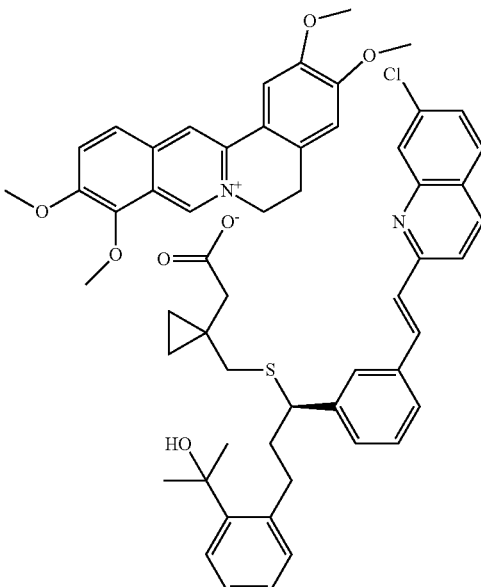
Compound 9
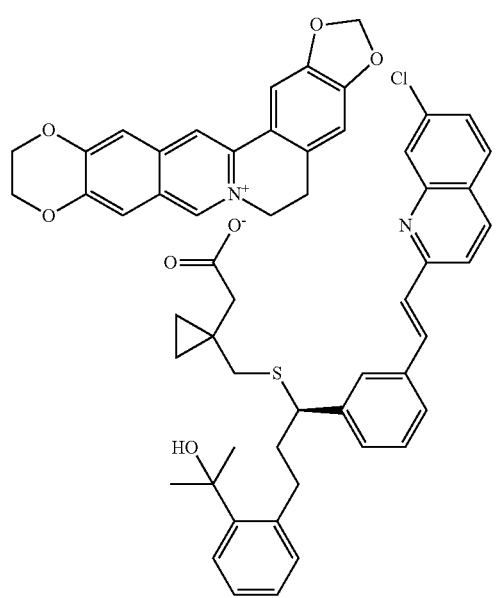
Compound 11
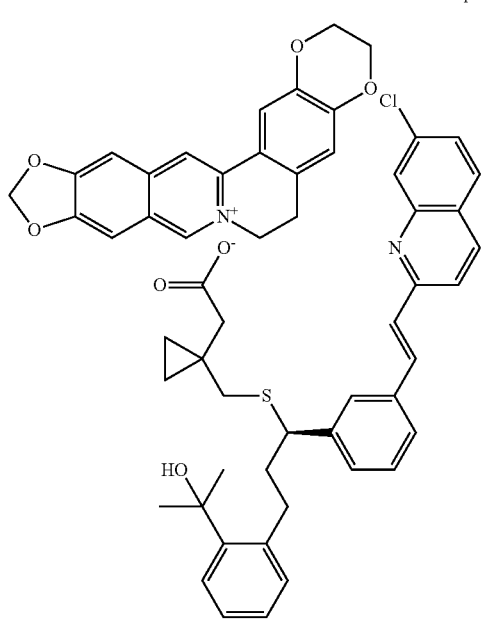

Compound 12

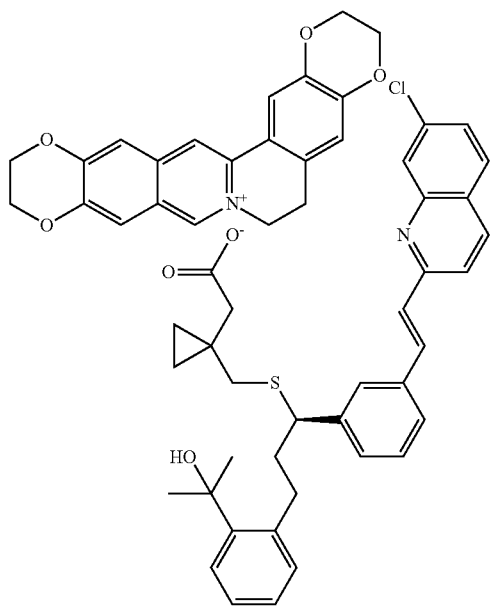

Compound 13

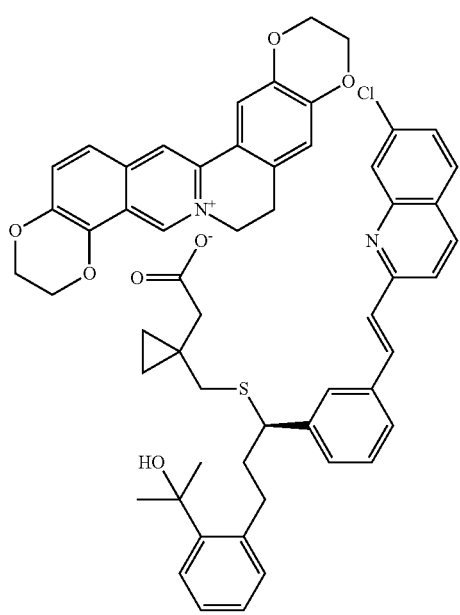

Compound 14

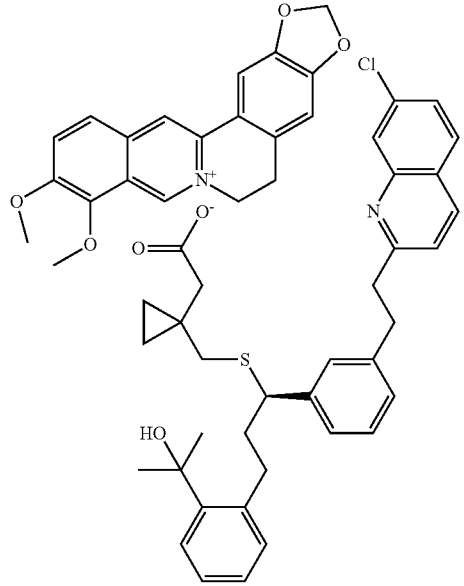

Compound 15

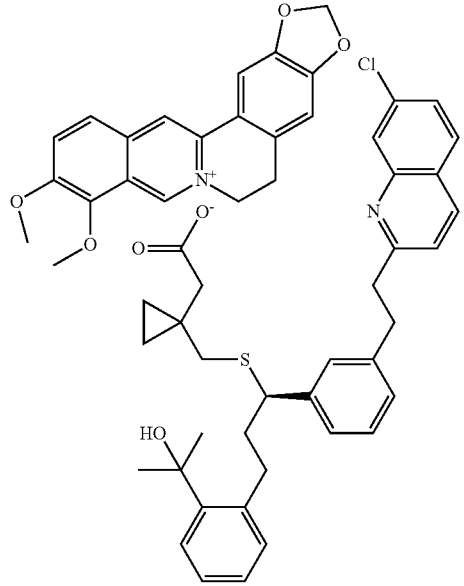

17. A synthesis method for the quaternary ammonium salt conjugated compound, the solvate, the enantiomer and the isotope substitution according to any one of claims claim 1, comprising the following steps:
  1) preparation of various free berberine alkaloid acetone addition products: weighing berberine alkaloid quaternary ammonium salt compounds of various acid radicals on demand and placing in a reaction flask, adding an inorganic base, then adding acetone dropwise, and stirring for reaction until the raw materials are completely reacted; performing suction filtration on the reaction mixture, washing a filter cake with water until neutral, and drying to obtain various free berberine alkaloid acetone addition products; and
  2) preparation of the quaternary ammonium salt conjugated compound, solvate or composition: weighing montelukast on demand and placing in a reaction flask, adding ethyl acetate to dissolve fully, and then adding an 8-acetonyl dihydroberberine alkaloid compound for reaction under stirring until the raw materials are completely reacted, followed by concentration under reduced pressure or crystallization; or adding an appropriate anti-solvent to the reaction mixture to obtain a berberine montelukast double salt composition.

18. A pharmaceutical composition, wherein the pharmaceutical composition comprises a therapeutically effective amount of at least one of the quaternary ammonium salt conjugated compound or the pharmaceutically acceptable salt, the solvate, the composition, the enantiomer and the isotope substitution or the double salt thereof according to any one of claims claim 1 or a pharmaceutically acceptable carrier or excipient.

19. A method for prevention or treatment of diseases related to inflammation, immunity, infection, allergy, metabolism and others, comprising: administering a patient with a preventively or therapeutically effective amount of at least one of the quaternary ammonium salt conjugated compound or the therapeutically acceptable salt, the solvate, the composition, the enantiomer and the isotope substitution or the double salt thereof according to claim 1.

20. A berberine montelukast double salt composition, wherein the berberine montelukast double salt composition is prepared into a clinically acceptable pharmaceutical preparation by taking a double salt of the quaternary ammonium salt conjugated compound according to any one of claims claim 1 as an effective ingredient and adding appropriate adjuvants and carriers.

\* \* \* \* \*

UNITED STATES PATENT AND TRADEMARK OFFICE
CERTIFICATE OF CORRECTION

| | | |
|---|---|---|
| PATENT NO. | : 12,221,418 B2 | Page 1 of 1 |
| APPLICATION NO. | : 18/708597 | |
| DATED | : February 11, 2025 | |
| INVENTOR(S) | : Wei Chen | |

It is certified that error appears in the above-identified patent and that said Letters Patent is hereby corrected as shown below:

In the Specification

Column 33, Line 15, replace "5'-GGTCCTAAGCAGTTGGTGGT-3'" with
-- 5'-GGTGCTAAGCAGTTGGTGGT-3' --.

Signed and Sealed this
Eighteenth Day of March, 2025

Coke Morgan Stewart
*Acting Director of the United States Patent and Trademark Office*

```
                         SEQUENCE LISTING

Sequence total quantity: 10
SEQ ID NO: 1            moltype = RNA   length = 23
FEATURE                 Location/Qualifiers
source                  1..23
                        mol_type = other RNA
                        organism = synthetic construct
SEQUENCE: 1
cgtgagtccc attaagatgg agt                                                23

SEQ ID NO: 2            moltype = RNA   length = 23
FEATURE                 Location/Qualifiers
source                  1..23
                        mol_type = other RNA
                        organism = synthetic construct
SEQUENCE: 2
cccgacagtg gatatagaac aga                                                23

SEQ ID NO: 3            moltype = RNA   length = 20
FEATURE                 Location/Qualifiers
source                  1..20
                        mol_type = other RNA
                        organism = synthetic construct
SEQUENCE: 3
tgagagtagt gaggaacaag                                                    20

SEQ ID NO: 4            moltype = RNA   length = 19
FEATURE                 Location/Qualifiers
source                  1..19
                        mol_type = other RNA
                        organism = synthetic construct
SEQUENCE: 4
cgcagaatga gatgagttg                                                     19

SEQ ID NO: 5            moltype = RNA   length = 22
FEATURE                 Location/Qualifiers
source                  1..22
                        mol_type = other RNA
                        organism = synthetic construct
SEQUENCE: 5
tgtcactgct actgctgctg ag                                                 22

SEQ ID NO: 6            moltype = RNA   length = 22
FEATURE                 Location/Qualifiers
source                  1..22
                        mol_type = other RNA
                        organism = synthetic construct
SEQUENCE: 6
ggtgaggtgg atcggttgta gt                                                 22

SEQ ID NO: 7            moltype = RNA   length = 22
FEATURE                 Location/Qualifiers
source                  1..22
                        mol_type = other RNA
                        organism = synthetic construct
SEQUENCE: 7
cctctctcta atcagccctc tg                                                 22
```

```
SEQ ID NO: 8             moltype = RNA    length = 21
FEATURE                  Location/Qualifiers
source                   1..21
                         mol_type = other RNA
                         organism = synthetic construct
SEQUENCE: 8
gaggacctgg gagtagatga g                                              21

SEQ ID NO: 9             moltype = RNA    length = 20
FEATURE                  Location/Qualifiers
source                   1..20
                         mol_type = other RNA
                         organism = synthetic construct
SEQUENCE: 9
atgttcgtca tgggtgtgaa                                                20

SEQ ID NO: 10            moltype = RNA    length = 20
FEATURE                  Location/Qualifiers
source                   1..20
                         mol_type = other RNA
                         organism = synthetic construct
SEQUENCE: 10
ggtgctaagc agttggtggt                                                20
```